US011186290B2

(12) United States Patent
Ito et al.

(10) Patent No.: US 11,186,290 B2
(45) Date of Patent: Nov. 30, 2021

(54) EMOTION INFERENCE DEVICE AND EMOTION INFERENCE SYSTEM

(71) Applicant: HONDA MOTOR CO., LTD., Tokyo (JP)

(72) Inventors: Atsushi Ito, Wako (JP); Yasumasa Matsui, Tokyo (JP); Kohei Matsuura, Wako (JP); Akiko Sakai, Wako (JP); Kimihiro Yonekawa, Tokyo (JP)

(73) Assignee: HONDA MOTOR CO., LTD., Tokyo (JP)

(*) Notice: Subject to any disclaimer, the term of this patent is extended or adjusted under 35 U.S.C. 154(b) by 291 days.

(21) Appl. No.: 16/345,018

(22) PCT Filed: Sep. 29, 2017

(86) PCT No.: PCT/JP2017/035631
§ 371 (c)(1),
(2) Date: Apr. 25, 2019

(87) PCT Pub. No.: WO2018/092436
PCT Pub. Date: May 24, 2018

(65) Prior Publication Data
US 2019/0276037 A1 Sep. 12, 2019

(30) Foreign Application Priority Data
Nov. 16, 2016 (JP) .............................. JP2016-223096

(51) Int. Cl.
B60W 40/09 (2012.01)
B60W 10/06 (2006.01)
(Continued)

(52) U.S. Cl.
CPC ............. B60W 40/09 (2013.01); A61B 5/167 (2013.01); A61B 5/18 (2013.01); B60W 10/06 (2013.01);
(Continued)

(58) Field of Classification Search
CPC .. B60W 40/09; B60W 10/06; B60W 2540/21; B60W 2540/043;
(Continued)

(56) References Cited

U.S. PATENT DOCUMENTS

2008/0096533 A1  4/2008  Manfredi et al.
2014/0192134 A1* 7/2014  Jung ...................... H04N 7/147
                                            348/14.02
(Continued)

FOREIGN PATENT DOCUMENTS

GB    2528083      1/2016
JP    2015-064584  4/2015
(Continued)

OTHER PUBLICATIONS

International Preliminary Report on Patentability dated May 31, 2019, 5 pages.
(Continued)

Primary Examiner — Rodney A Butler
(74) Attorney, Agent, or Firm — Rankin, Hill & Clark LLP

(57) ABSTRACT

An emotion inference device and an emotion inference system that are capable of inferring a user's emotion with higher precision. A motorcycle includes an individual personality that is configured on the basis of information on a user from a plurality of products associated with the user, connected to a communication network, and including the motorcycle, an automobile, a rice cooker, a vacuum cleaner, a television receiver, and a refrigerator, the individual personality forms a base personality, and the motorcycle includes an emotion detecting section that detects an emotion.

7 Claims, 16 Drawing Sheets

(51) Int. Cl.
*G06K 9/00* (2006.01)
*G06N 5/04* (2006.01)
*G10L 25/63* (2013.01)
*B60W 40/08* (2012.01)
*B60W 50/00* (2006.01)
*G08G 1/16* (2006.01)
*G06T 7/00* (2017.01)
*G06F 3/01* (2006.01)
*A61B 5/18* (2006.01)
*A61B 5/16* (2006.01)
*G09B 19/16* (2006.01)

(52) U.S. Cl.
CPC ........ *B60W 40/08* (2013.01); *B60W 50/0097* (2013.01); *G06F 3/017* (2013.01); *G06K 9/00302* (2013.01); *G06K 9/00335* (2013.01); *G06N 5/04* (2013.01); *G06T 7/0014* (2013.01); *G08G 1/16* (2013.01); *G09B 19/16* (2013.01); *G10L 25/63* (2013.01); *B60W 2040/0872* (2013.01); *B60W 2050/0029* (2013.01); *B60W 2420/42* (2013.01); *B60W 2420/54* (2013.01); *B60W 2540/043* (2020.02); *B60W 2540/21* (2020.02); *B60W 2540/22* (2013.01); *B60W 2556/10* (2020.02); *G06F 2203/011* (2013.01)

(58) Field of Classification Search
CPC ......... B60W 2420/54; B60W 2540/22; B60W 2040/0872; B60W 2050/0029; B60W 2530/14; B60W 2420/42; B60W 40/08; B60W 50/0097; G06T 7/0014; A61B 5/18; A61B 5/167; G09B 19/16; G08G 1/16; G06K 9/00335; G06K 9/00302; G06N 5/04; G10L 25/63; G06F 2203/011; G06F 3/017

See application file for complete search history.

(56) References Cited

U.S. PATENT DOCUMENTS

| | | |
|---|---|---|
| 2014/0359439 A1 | 12/2014 | Lyren |
| 2015/0358416 A1* | 12/2015 | Gariepy ................. G06Q 50/01 709/206 |
| 2015/0371663 A1* | 12/2015 | Gustafson ............... G06F 3/167 704/270.1 |
| 2016/0055370 A1* | 2/2016 | Garcia ............... G06K 9/00288 382/118 |
| 2017/0017838 A1* | 1/2017 | Biswas .............. G06K 9/00302 |

FOREIGN PATENT DOCUMENTS

| | | |
|---|---|---|
| JP | 2016-137200 | 8/2016 |
| JP | 2016-147006 A | 8/2016 |
| WO | 2016/005289 A1 | 1/2016 |

OTHER PUBLICATIONS

European Office Action dated Aug. 14, 2020, 4 pages.
Japanese Office Action with English translation dated Mar. 24, 2020, 10 pages.
European Search Report dated Oct. 22, 2019, 8 pages.
International Search Report, 1 page.
Indian Office Action dated Mar. 24, 2021, 8 pages.

* cited by examiner

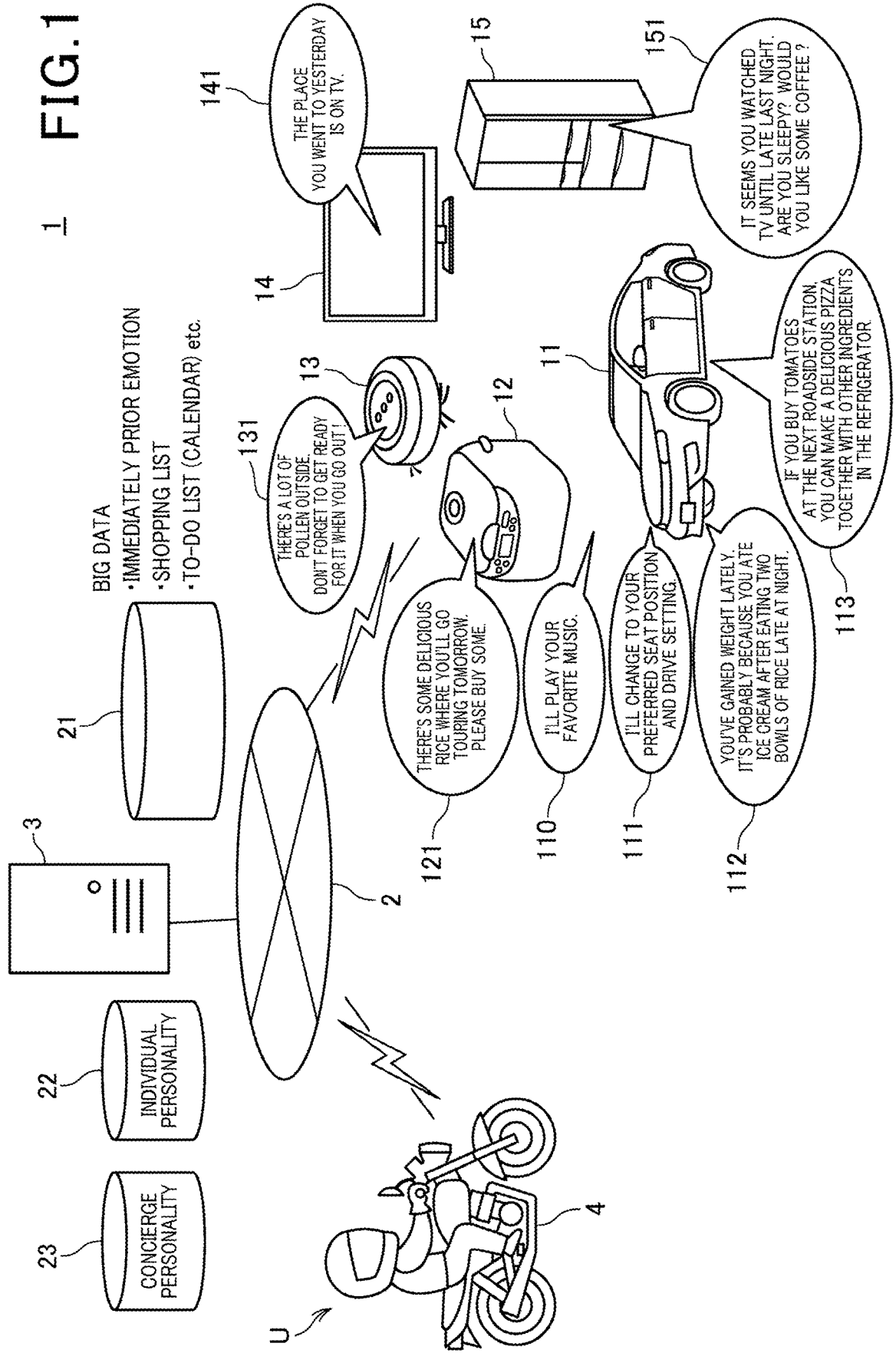

FIG.2

| DEVICE CATEGORY | DETECTION VALUE | TYPE OF CORRESPONDING ACTION |
|---|---|---|
| MOTORCYCLE | DRIVE CONTROL | SEAT HEIGHT ADJUSTMENT |
| | | DRIVE CONTROL |
| | VOICE | VOICE (CONVERSATION) |
| AUTOMOBILE | DRIVE CONTROL | VEHICLE HEIGHT |
| | WEIGHT | DRIVE CONTROL |
| | VOICE | VOICE (CONVERSATION) |
| REFRIGERATOR | NUMBER OF OPENING/CLOSING TIMES | VOICE (CONVERSATION) |
| | CONTENT | |
| | VOICE | |
| RICE COOKER | USE FREQUENCY | VOICE (CONVERSATION) |
| | OPERATION MENU HISTORY | |
| | VOICE | |
| SELF-PROPELLED VACUUM CLEANER | COLLECTED DUST AMOUNT | VOICE (CONVERSATION) |
| | VOICE | |
| TELEVISION RECEIVER | WATCHING HISTORY | PROGRAM SELECTION |
| | VOICE | VOICE (CONVERSATION) |
| AIRPLANE (SEAT) | VOICE | SEAT POSITION ADJUSTMENT |
| | | VOICE (CONVERSATION) |
| FITTING ROOM | VOICE | VOICE (CONVERSATION) |

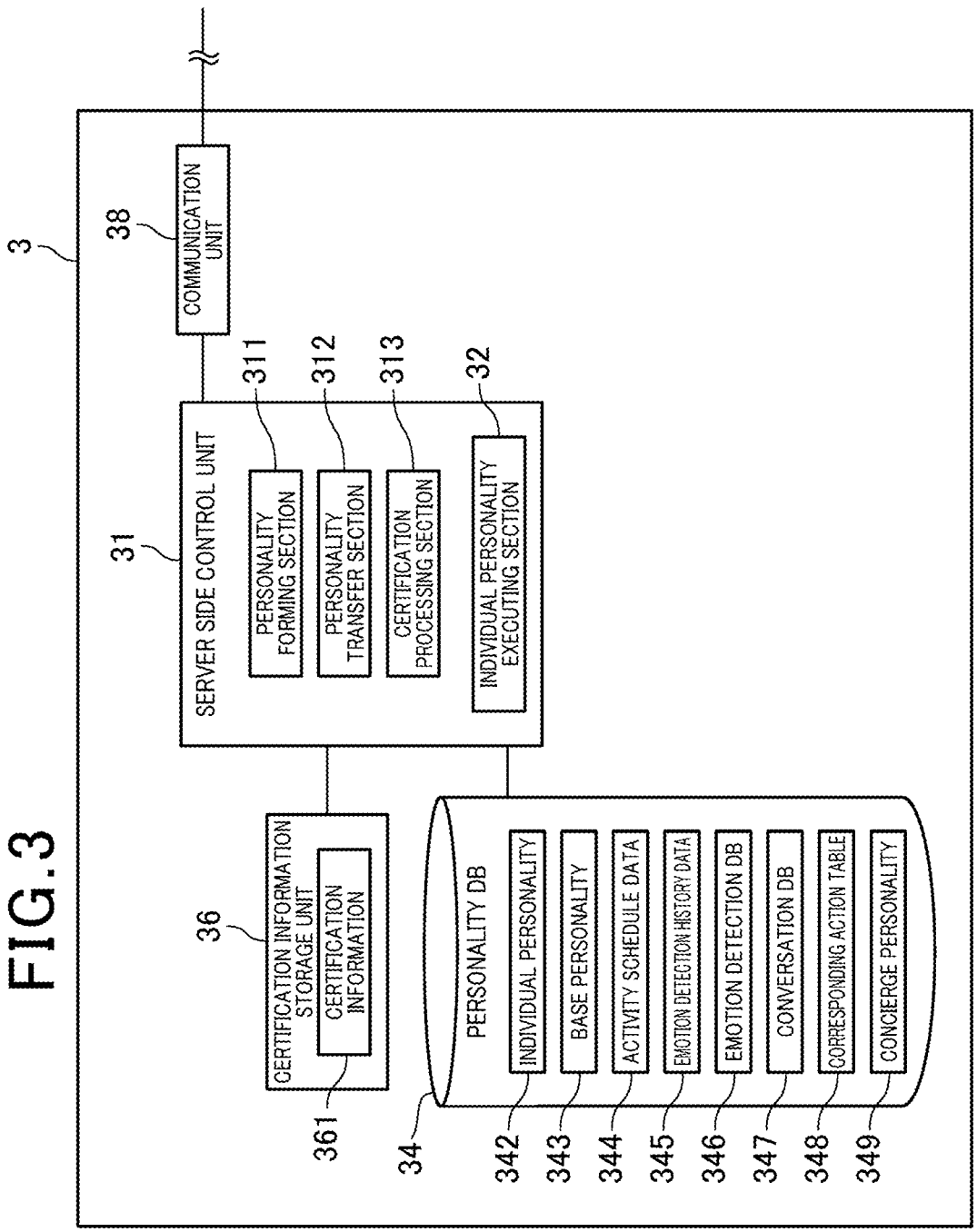

FIG.5

| DETECTION VALUE | PARAMETER FOR EMOTION DETECTION |
|---|---|
| VOICE | CONVERSATION/MONOLOGUE/CONTENT OF MONOLOGUE |
| THROTTLE OPENING DEGREE | CHANGE OF THROTTLE OPENING DEGREE |
| BRAKE OPERATION AMOUNT | CHANGE OF BRAKE OPERATION AMOUNT |
| G SENSOR DETECTION VALUE | G SENSOR DETECTION VALUE |
| CAMERA CAPTURED IMAGE | USER'S FACIAL EXPRESSION |

| EMOTION ATTRIBUTE | USUAL CORRESPONDING ACTION | ACTION FOR QUIETING DOWN EMOTION | ACTION FOR DRIVING |
|---|---|---|---|
| ANGER | ACTION A-1 | ACTION A-2 | ACTION A-3 |
| SADNESS | ACTION S-1 | ACTION S-2 | ACTION S-3 |
| INSIGNIFICANCE | ACTION I-1 | ACTION I-2 | ACTION I-3 |
| TIREDNESS | ACTION T-1 | ACTION T-2 | ACTION T-3 |
| PLEASURE | ACTION H-1 | ACTION H-2 | ACTION H-3 |

| ACTION | ACTION DETAILS | CONTROL TARGET | ACTION CONTENT |
|---|---|---|---|
| ACTION A-2 | ENGINE OUTPUT | THROTTLE DEVICE CONTROL PARAMETER | LOWER OPENING DEGREE |
| | | FUEL INJECTION MAP | LOWER OUTPUT |
| | | IGNITION TIMING PARAMETER | LOWER OUTPUT |
| | TORQUE CONTROL | FUEL INJECTION MAP | LOWER TORQUE |
| | | IGNITION TIMING PARAMETER | LOWER TORQUE |
| | THROTTLE OPENING DEGREE LIMITATION | THROTTLE DEVICE CONTROL PARAMETER | LIMITATION VALUE: LOW |
| | ABS | BRAKE CONTROL PARAMETER | COPE WITH HIGH SPEED |
| | SUSPENSION SETTING | PARAMETER FOR SUSPENSION ADJUSTMENT | IMPORTANCE TO RIDE COMFORT |
| | METER PANEL DISPLAY | METER PANEL DISPLAY COLOR | RELAXING COLOR |
| | VOICE | OUTPUT VOICE | RELAXING CONVERSATION |
| ⋮ | ⋮ | ⋮ | ⋮ |

488a

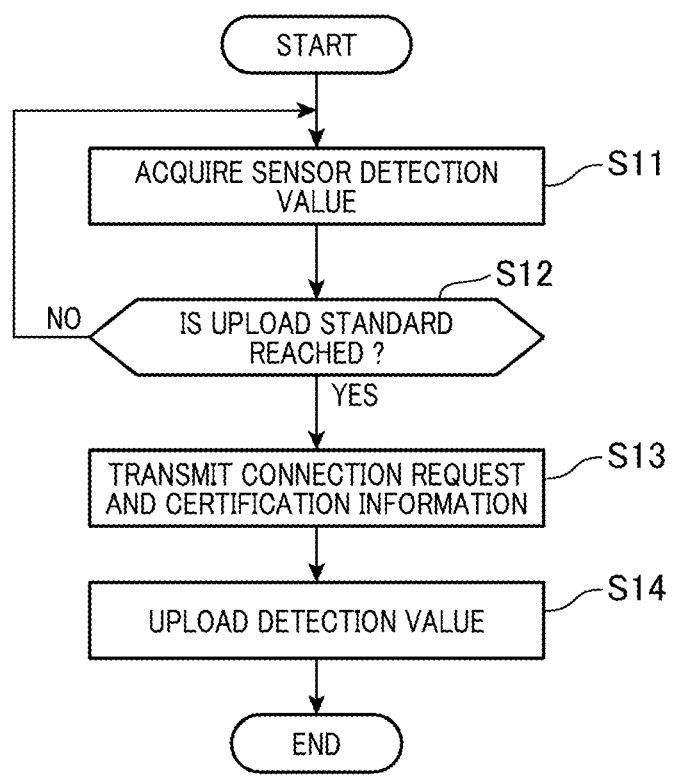

EMOTION INFERENCE DEVICE AND EMOTION INFERENCE SYSTEM

TECHNICAL FIELD

The present invention relates to an emotion inference device and an emotion inference system.

BACKGROUND ART

Heretofore, a device that infers an emotion of a driver is known (e.g., see Patent Literature 1). The device described in Patent Literature 1 infers a driver's emotions and mentalities when driving support is performed during driving.

CITATION LIST

Patent Literature

[Patent Literature 1]
Japanese Patent Laid Open No. 2015-64584

SUMMARY OF INVENTION

Technical Problem

A device described in Patent Literature 1 infers a driver's emotion on the basis of information obtained from a vehicle, such as information on a driving operation. However, a time when a person drives the vehicle is a limited time in a day. Even if the driver's emotion is inferred from the driving operation or the like in this limited time, there is a limit to precision of the inference. Furthermore, this is not limited to the vehicle, and there is also a similar problem in a case where an emotion of a user who uses a device is inferred on the basis of an operation and the like during the use of the device.

The present invention has been developed in view of the above described situations, and an object of the invention is to provide an emotion inference device and an emotion inference system which are capable of inferring a user's emotion with higher precision.

Solution to Problem

In this description, all contents of Japanese Patent Application No. 2016-223096 filed on Nov. 16, 2016 are included.

To achieve the above object, according to an aspect of the present invention, an emotion inference device includes an individual personality (482) that is configured on the basis of information on a user (U) from a plurality of products (4, 11, 12, 13, 14, and 15) associated with the user (U) and connected to a communication network (2), the individual personality (482) forming a base personality (483), and the device includes an emotion detecting section (464) that detects an emotion.

According to another aspect of the present invention, an emotion inference device includes an individual personality (482) that is formed by machine learning based on user information collected from a plurality of products (4, 11, 12, 13, 14, and 15) used by a user (U), the individual personality (482) forming a base personality (483), and the device includes an emotion detecting section (464) that detects an emotion of the user (U).

According to the configuration of the present invention, the emotion can be detected with high precision by the individual personality configured on the basis of the information from the plurality of products. For example, when the individual personality is configured on the basis of the information from the plurality of products that are different in the time to be used by the user, the information collected or detected for a longer period of time can be reflected in the individual personality as compared with a case where a user's emotion is inferred from a single product. By use of this individual personality, the emotion can be detected with higher precision than by use of information obtained from the single product. Furthermore, as to a specific product, an emotion before the product is associated with the user can be detected.

Furthermore, in the emotion inference device according to another aspect of the present invention, the emotion detecting section (464) may be configured to compare the emotion of the base personality (483) with the emotion of the individual personality (482) at the moment, and detect an emotion attribute.

According to this configuration, it is possible to detect the emotion with higher precision by comparing the emotion of the base personality to the emotion of the individual personality at the moment and additionally taking a tendency and a characteristic of the emotion into consideration. For example, when there is a tendency that a specific emotion easily appears in the emotion of the user, a state where the specific emotion is frequently detected can be avoided, and the emotion can be detected with higher precision by use of a standard adapted to an individual emotion tendency.

Furthermore, the emotion inference device according to another aspect of the present invention may include an action control section (470) that controls an action to direct the emotion to the emotion of the base personality (483), when a predetermined change or greater is present in the emotion detected by the emotion detecting section (464).

According to this configuration, when the individual personality performs the action to direct the user's emotion toward the emotion of the base personality, it is possible to take the tendency or the characteristic of the user's emotion into consideration and to act on the user's emotion. In consequence, for example, the user's emotion can be quieted down.

Additionally, the emotion inference device according to another aspect of the present invention may include an emotion accumulation unit (485) that accumulates the emotion detected by the emotion detecting section (464), an activity schedule table (484) that shows an activity schedule of the user (U), and an emotion change cause inferring section (469) that infers an emotion change cause from at least the emotion accumulated in the emotion accumulation unit (485) or a future schedule shown in the activity schedule table (484) of the user (U), when there is a large change in the emotion of the user (U).

According to this configuration, a cause that changes the user's emotion or a cause that influences the emotion can be inferred from the future schedule. In consequence, it is possible to cope with the cause that changes the emotion or the cause that influences the emotion, so that the user's emotion is influenced.

Furthermore, in the emotion inference device according to another aspect of the present invention, the cause inferred by the emotion change cause inferring section (469) may be also accumulated when accumulating the emotion in the emotion accumulation unit (485).

According to this configuration, data concerning the tendency of the user's emotion and the cause can be collected by accumulating the cause that changes the user's emotion or the cause that influences the emotion. For example, when a computer is used as an emotion inference unit, the collected data can be used as data to be learned by this computer.

Additionally, in the emotion inference device according to another aspect of the present invention, the action control section (470) may be configured to cope with the cause inferred by the emotion change cause inferring section (469) and to control an action that directs the emotion to the emotion of the base personality (483).

According to this configuration, the action that directs the user's emotion to the emotion of the base personality can be performed on the basis of the cause that changes the user's emotion or the cause that influences the emotion, the cause being accumulated in the emotion accumulation unit. In consequence, it is possible to take the tendency or the characteristic of the user's emotion into consideration and to more effectively act on the user's emotion.

Furthermore, in the emotion inference device according to another aspect of the present invention, one of the products (4, 11, 12, 13, 14, and 15) is a vehicle (4), the vehicle (4) includes a driving tendency judging section (464) that judges a driving tendency, the driving tendency judging section (464) distinguishes at least between patient driving and impatient driving, and judges whether or not the emotion influences the driving, from at least an immediately prior emotion and the activity schedule shown in the activity schedule table (484) of the user (U), when it is judged that the driving of the user (U) is the impatient driving, and when it is judged that the driving is influenced, the action control section (470) performs an action that directs the emotion so as to eliminate the influence on the driving.

According to this configuration, the device acts on the user to direct the user's emotion so that the influence on the driving is eliminated, and it is possible to achieve elimination or alleviation of a factor that influences the driving of the vehicle.

Additionally, in the emotion inference device according to another aspect of the present invention, the emotion that influences the driving may include any one of anger, anxiety, sorrow, and insecurity.

According to this configuration, when it is detected that the user's emotion is an emotion such as the anger, the anxiety, the sorrow, or the insecurity, it is possible to achieve elimination or alleviation of an influence of such an emotion on the driving.

Furthermore, in the emotion inference device according to another aspect of the present invention, the individual personality (482) may be configured on the basis of artificial intelligence.

According to this configuration, since the individual personality that is the artificial intelligence is configured on the basis of the information from the plurality of products, the emotion can be detected with high precision by the individual personality.

Additionally, in the emotion inference device according to another aspect of the present invention, the individual personality (482) may be configured to imitate the emotion or emotion change of the user (U), and the emotion detecting section (464) may be configured to detect the emotion of the individual personality (482).

According to this configuration, the user's emotion or emotion change can be easily detected by detecting the emotion of the individual personality. Furthermore, the individual personality is configured on the basis of the information from the plurality of products, so that the user's emotion can be detected with higher precision.

Furthermore, to achieve the above object, according to an aspect of the present invention, an emotion inference system includes a vehicle (4) connected to a communication network (2), a plurality of products (11, 12, 13, 14, and 15) associated with a user (U) and connected to the communication network (2), an individual personality (482) that is configured on the basis of information on the user (U) from the plurality of products (11, 12, 13, 14, and 15), the individual personality (482) forming a base personality (483), and an emotion detecting section (464) that detects an emotion, wherein the vehicle includes the individual personality (482) and the emotion detecting section (464).

According to the configuration of the present invention, the vehicle can detect the emotion with high precision by the individual personality configured on the basis of the information from the plurality of products. Consequently, the emotion can be detected with higher precision by use of not only information collected or detected during driving of the vehicle but also the information collected or detected by more products over a long time. Additionally, it is also possible to detect the emotion of the user in a state where the user is not associated with the vehicle.

Advantageous Effects of Invention

In an emotion inference device according to an aspect of the present invention, an emotion can be detected with high precision by an individual personality that is configured on the basis of information from a plurality of products. Furthermore, as to a specific product, the emotion before the product is associated with a user can be detected.

Additionally, in the above aspect of the present invention, an emotion detecting section may be configured to compare an emotion of a base personality with an emotion of the individual personality at the moment, and detect an emotion attribute. In this case, it is possible to detect the emotion with higher precision by additionally taking a tendency and a characteristic of the emotion into consideration.

In addition, the emotion inference device according to another aspect of the present invention may include an action control section to control an action that directs the emotion to the emotion of the base personality when a predetermined change or greater is present in the emotion detected by the emotion detecting section. In this case, it is possible to take the tendency and characteristic of the user's emotion into consideration and to act on the user's emotion.

Furthermore, the above emotion inference device according to another aspect of the present invention may include an emotion accumulation unit that accumulates the emotion detected by the emotion detecting section, an activity schedule table that shows an activity schedule of the user, and an emotion change cause inferring section that infers an emotion change cause from at least the emotion accumulated in the emotion accumulation unit or a future schedule shown in the activity schedule table of the user when there is a large change in the user's emotion. In this case, a cause that changes the user's emotion or a cause that influences the emotion can be inferred from the future schedule, and it is possible to cope with the cause so that the user's emotion is influenced.

Additionally, in the above aspect of the present invention, the cause inferred by the emotion change cause inferring section may be also accumulated when accumulating the emotion in the emotion accumulation unit. In this case, data concerning the tendency of the user's emotion and the cause can be collected.

Furthermore, in the above aspect of the present invention, the action control section may be configured to control the action that directs the emotion to the emotion of the base personality in accordance with the cause inferred by the emotion change cause inferring section. In this case, it is possible to take the tendency or the characteristic of the user's emotion into consideration and to more effectively act on the user's emotion.

Additionally, in the above aspect of the present invention, one of the products is a vehicle, the vehicle includes a driving tendency judging section that judges a driving tendency, the driving tendency judging section distinguishes at least between patient driving and impatient driving, and judges whether or not the emotion influences the driving, from at least an immediately prior emotion and the activity schedule shown in the activity schedule table of the user when it is judged that the driving of the user is the impatient driving, and when it is judged that the driving is influenced, the action control section performs the action that directs the emotion to eliminate the influence on the driving. In this case, it is possible to achieve elimination or alleviation of a factor that influences the driving of the vehicle.

In addition, according to the above aspect of the invention, the emotion that influences the driving may include any one of anger, anxiety, sorrow, and insecurity. In this case, when it is detected that the user's emotion is an emotion such as the anger, the anxiety, the sorrow, or the insecurity, it is possible to achieve elimination or alleviation of an influence of such an emotion on the driving.

Furthermore, in the above aspect of the present invention, the individual personality may be configured on the basis of artificial intelligence. In this case, the emotion can be detected with high precision by the individual personality.

Additionally, in the above aspect of the present invention, the individual personality may be configured to imitate the emotion or emotion change of the user, and the emotion detecting section may be configured to detect the emotion of the individual personality. In this case, the user's emotion or emotion change can be easily detected with higher precision.

Furthermore, in an emotion inference system according to an aspect of the present invention, a vehicle can detect an emotion with high precision by an individual personality that is configured on the basis of information from a plurality of products. Furthermore, it is also possible to detect the emotion in a state where the user is not associated with the vehicle.

BRIEF DESCRIPTION OF DRAWINGS

FIG. 1 is a schematic view of an emotion inference system according to an embodiment of the present invention.

FIG. 2 is a diagram showing a specific example of an operation of each device in the emotion inference system.

FIG. 3 is a function block diagram of a server.

FIG. 5 is a schematic diagram showing a configuration example of emotion detection setting data.

FIG. 7 is a schematic diagram showing a configuration example of a correspondence action table.

FIG. 8 is a schematic diagram showing a configuration example of the correspondence action table.

FIG. 9 is a flowchart showing an operation of the device constituting the emotion inference system.

DESCRIPTION OF EMBODIMENTS

Figure 4:
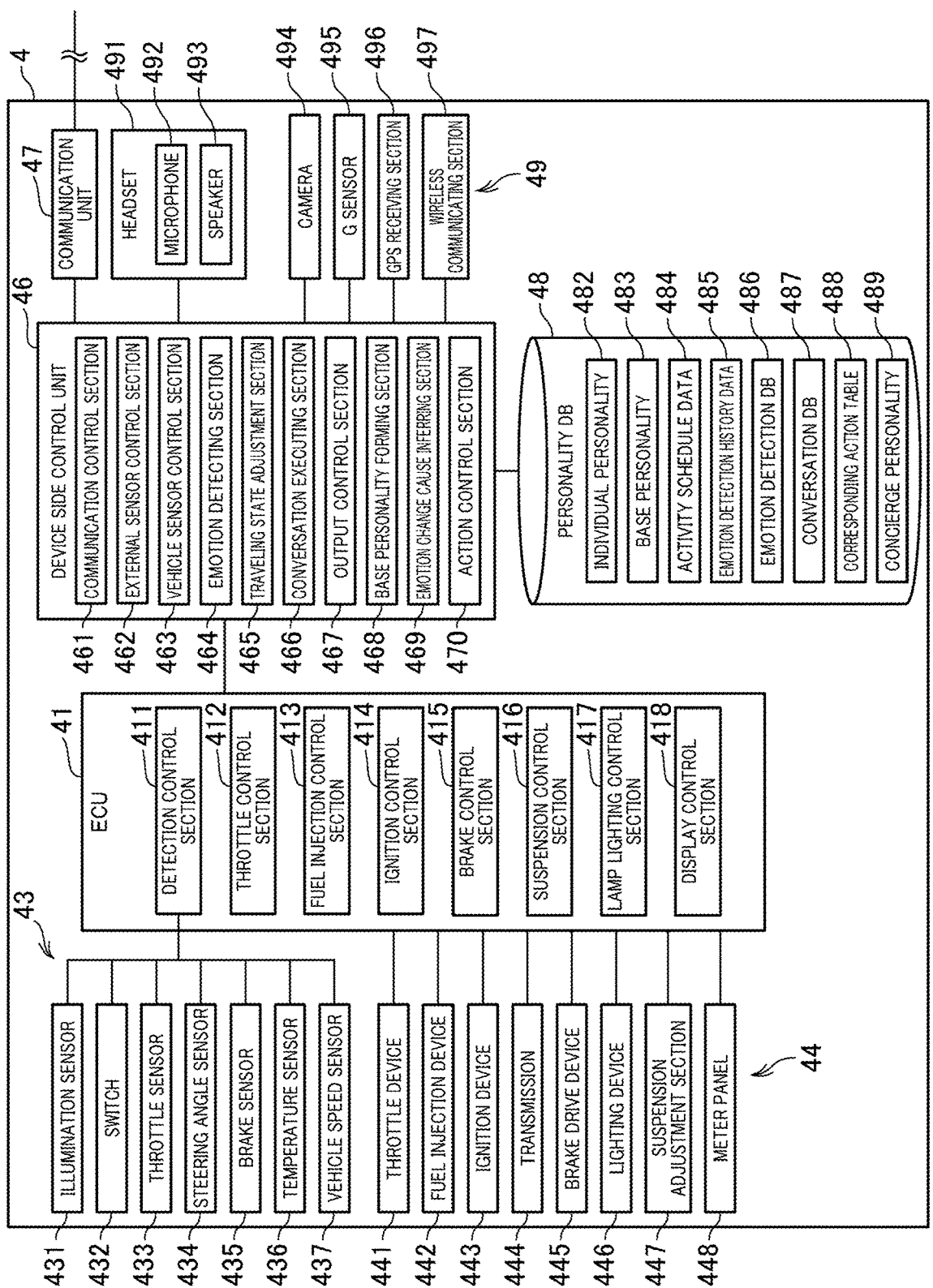
FIG. 4 is a function block diagram of a motorcycle.

Hereinafter, embodiments of the present invention will be described with reference to the drawings.

FIG. 1 is a schematic view of an emotion inference system 1.

The emotion inference system 1 includes a plurality of devices including a motorcycle 4 and a server 3 which are connected to a communication network 2. There are not any special restrictions on a category, use application, structure, and the like of any device that is provided in the emotion inference system 1 and is for use by a user U. In the present embodiment, in addition to the motorcycle 4, an automobile 11, a rice cooker 12, a vacuum cleaner 13, a television receiver 14, and a refrigerator 15 are exemplified.

Respective devices of the motorcycle 4 (a vehicle), the automobile 11 (a vehicle), the rice cooker 12, the vacuum cleaner 13, the television receiver 14, and the refrigerator 15 are connected to the communication network 2, respectively. These respective devices execute communication with the server 3 via the communication network 2, and transmit and receive data. Furthermore, the respective devices execute communication with one another via the communication network 2.

Each of these devices functions as an emotion inference device of the present invention.

The communication network 2 is a network via which a plurality of computers can execute communication, and is, for example, a wide area communication network. The communication network 2 may be an open network such as the Internet, or a closed communication network. When the communication network 2 is the open network, the server 3 and respective devices which constitute the emotion inference system 1 may execute secure communication on the communication network 2 by use of a virtual private network (VPN) technology or the like. Furthermore, an example of the communication network 2 is a communication line such as a public telephone line or a leased line, and the communication network may include various network equipment, such as a router, a gateway server, a switch, and a bridge which relay or control the communication via the communication line. Additionally, a communication protocol for use in data communication via the communication network 2 is not limited.

The server 3 is not limited to a server including a single computer, and may include, for example, a network computer (a so-called cloud computer).

The user U corresponds to oneself mentioned in the present invention. The oneself is a person (human) of a target itself an emotion of which is inferred by the emotion inference system 1, or the motorcycle 4, the automobile 11, the rice cooker 12, the vacuum cleaner 13, the television receiver 14, or the refrigerator 15 that constitutes the emotion inference system 1. In the present embodiment, the user U is a person who drives the motorcycle 4. It is not essential for the user U to drive the motorcycle 4, and is shown as a preferable example in the present embodiment. An example of the user U is a user who uses at least a plurality of devices among the motorcycle 4, the automobile 11, the rice cooker 12, the vacuum cleaner 13, the television receiver 14, and the refrigerator 15 which constitute the emotion inference system 1. In the present embodiment, the motorcycle 4, the automobile 11, the rice cooker 12, the vacuum cleaner 13, the television receiver 14, and the refrigerator 15 for use by one user U estimate an emotion of the user U. The user U regularly or temporarily uses the motorcycle 4, the automobile 11, the rice cooker 12, the vacuum cleaner 13, the television receiver 14, and the refrigerator 15 which constitute the emotion inference system 1, but the user U is not restricted to possessing of the above devices. The user U may be a person who rents the above device for use. For example, the automobile 11 may be a rented car that is temporarily rented and used by the user U.

In the emotion inference system 1, the motorcycle 4, the automobile 11, the rice cooker 12, the vacuum cleaner 13, the television receiver 14, and the refrigerator 15 are the devices associated with the user U. The motorcycle 4 is a motorcycle to be driven or ridden by the user U. The automobile 11 is a car for use by the user U. A mode of the use of the automobile 11 is not limited to a mode in which the user U drives the automobile, and a mode in which a person different from the user U drives the automobile and the user U is on board as a passenger is also included in an application range of the present invention.

The rice cooker 12 is a rice cooker as one example of equipment for use in cooking by the user U. The rice cooker 12 may be replaced with other kitchenware such as a microwave, an electromagnetic cooker, an oven, or an electric water heater. The vacuum cleaner 13 is, for example, a self-propelled vacuum cleaner that executes cleaning in accordance with contents previously set by the user U as to time to execute the cleaning and a place of a target to be cleaned at. The television receiver 14 is one example of equipment with which the user U previews a video or music, and watches a television program. The refrigerator 15 is one example of equipment for use in storing cooking ingredients or the like by the user U.

These devices are specific examples of the device associated with the user U, and the target to which the present invention is applied is not limited to these devices.

Any of the respective devices constituting the emotion inference system 1 performs processing concerning the emotion of the user U, and therefore includes a computer. This computer may be a computer provided for each device to execute an original function, for example, an engine control unit (ECU) provided for the motorcycle 4 to execute an operation as the motorcycle, or a microcomputer provided for the rice cooker 12 to execute a cooking function. Furthermore, each device may include a computer for exclusive use in inferring the emotion of the user U and performing processing to cope with the inferred emotion.

In the present embodiment, each of the respective devices of the emotion inference system 1 achieves an individual personality 22. The individual personality 22 is a virtual personality that imitates the emotion or emotion change of the user U. The individual personality 22 is constructed in accordance with a computer program, behaves as a virtual human, and has an emotion that imitates the emotion of the user U as if the personality were an actual human. The emotion of the individual personality 22 is set to change similarly to the emotion of the user U. In other words, the individual personality 22 simulates (or emulates) the emotion of the user U. The individual personality 22 is executed by the computer when the computer executes the program constituting the individual personality 22. The program constituting the individual personality 22 may be a program that simulates a human emotion. Furthermore, the program may be a program that obtains an output value indicative of the human emotion, from a specific parameter, and may be the simple program having one-to-one correspondence between the parameter and the output value.

As one example in the present embodiment, the individual personality 22 is configured on the basis of artificial intelligence (AI). That is, the function of the individual personality 22 is achieved by all or several groups of technical elements belonging to or associated with an artificial intelligence technology. Examples of this type of technical element include various filtering, independent component analysis, a support vector machine (SVM), contour extraction and another image processing technology, pattern recognition (e.g., voice recognition, face recognition, and the like), natural language processing, knowledge information processing, reinforcement learning, Bayesian network, a self-organizing map (SOM), a neural network, deep learning, and the other machine learning.

In the emotion inference system 1, each device associated with the user U executes the program of the individual personality 22. Each device detects an operation or voice of the user U which is associated with the user U during the action of the individual personality 22, and collects a detection result. This detection result is sent as big data 21 to the server 3, and the individual personality 22 learns this big data 21. Thus, the individual personality 22 performs the learning, so that the individual personality 22 can imitate the emotion of the user U with high precision. Therefore, the emotion of the individual personality 22 is regarded as the emotion of the user U, and the current emotion of the individual personality 22 is detected, so that the emotion of the user U can be detected or inferred.

The emotion inference system 1 has a concierge personality 23. The concierge personality 23 is a virtual personality that performs communication (e.g., conversation) with the user U, like a human being. The user U performs the conversation with the concierge personality 23 that behaves as a virtual human being constructed on the basis of the computer program, as if the user were to perform the conversation with the actual human being. The concierge personality 23 can act in such a manner that the human being has some apprehension with the user U, and behaves as a personal adviser, an assistant, or a guide for the user U to provide aid, guide, support, or the like to the user U. For the purpose of giving a generic name to these roles, in the embodiment, a name of the concierge personality 23 is given. The concierge personality 23 can be referred to as, for example, a personal assistant in place of the term of concierge.

The computer executes the function of the concierge personality 23 when the computer executes the program that constitutes the concierge personality 23. The program constituting the concierge personality 23 may be a program that simulates the human emotion. Furthermore, the program may be a program that obtains an output value indicative of the human emotion from a specific parameter, and may be a simple program having one-to-one correspondence between the parameter and the output value.

The concierge personality 23 may be configured on the basis of the artificial intelligence (AI) in the same manner as in the individual personality 22. That is, a function of the concierge personality 23 may be achieved by all or several groups of technical elements belonging to or associated with an artificial intelligence technology in the same manner as in the individual personality 22.

The concierge personality 23 is not limited to a personality that performs conversation in voice with the user U, and the personality may control an action of the device for use by the user U, for example, as described later. The concierge personality 23 may perform the action including the conversation and/or the device control with respect to the user U so as to direct the emotion of the user U to a specific emotion. For example, the concierge personality 23 adjusts a behavior of the motorcycle 4 during driving of the motorcycle 4 by the user U, for example, as described later.

The respective devices of the motorcycle 4, the automobile 11, the rice cooker 12, the vacuum cleaner 13, the television receiver 14, and the refrigerator 15 of the emotion inference system 1 have a function of inferring the emotion of the user U in addition to an original function of each of the above described devices. These devices infer the emotion of the user U from data obtained from a history of an operation performed to the devices by the user U, contents of the conversation performed between the user U and each device, and the like. Furthermore, each device has a function of performing the conversation in the voice with the user U in accordance with the inferred emotion of the user U. For this function, each device includes a microphone that collects the voice of the user U, and a speaker which emits the voice.

FIG. 2 is a diagram showing specific examples of actions of the respective devices in the emotion inference system 1. Specifically, FIG. 2 shows an example of a detection value for use by each device of the emotion inference system 1 to infer the emotion of the user U, and an example of the action to be executed in accordance with the emotion of the user U.

For example, the motorcycle 4 uses, as the detection value to infer the emotion of the user U, a detection value concerning driving control in a case where the user U drives the motorcycle 4, and the voice of the user U. The automobile 11 uses, as the detection values to infer the emotion of the user U, a detection value concerning driving control in a case where the user U drives the automobile 11, a body weight of the user U which is detected by a weight sensor provided in the automobile 11, and the voice of the user U. Examples of the data concerning the driving control of the automobile 11 include a distance traveled, a traveling speed, a throttle opening, a steering angle, a brake operation amount, and a vehicle weight. Furthermore, the automobile 11 may perform position measurement by use of a global positioning system (GPS) or the like, thereby acquire data of a place of departure, a place of arrival, a place of transit, or the like, and acquire data concerning a place and time where refueling is performed, and may process these pieces of data as the data concerning the driving control.

The refrigerator 15 uses, as the detection values to infer the emotion of the user U, a number of times of opening and closing of a door, data concerning contents, and the voice of the user U. The rice cooker 12 uses, as the detection values to infer the emotion of the user U, a frequency of using the rice cooker 12 by the user U, a history of an item selected from an operation menu of the rice cooker 12 by the user U, and the voice of the user U. The vacuum cleaner 13 uses, as the detection values to infer the emotion of the user U, an amount of dust to be collected and the voice of the user U. The television receiver 14 uses, as the detection values to infer the emotion of the user U, watching histories including data of a broadcast station from which broadcasting is received by an operation of the user U, data of time when the broadcasting is received and an image is displayed, and the like, and the voice of the user U.

When the motorcycle 4 infers the emotion of the user U, the motorcycle 4 is controlled to act on the emotion of the user U. For example, as shown in FIG. 2, examples of the control in this case include adjustment of a seat height of the motorcycle 4, driving control, and an action of emitting the voice to the user U. Furthermore, the automobile 11 performs, as actions that act on the emotion of the user U, adjustment of a vehicle height, the driving control, the action of emitting the voice to the user U, and the like. The television receiver 14 performs, as actions that act on the emotion of the user U, an action of selecting a program and showing the program to the user U in addition to the emission of the voice to the user U. The rice cooker 12, the vacuum cleaner 13, and the refrigerator 15 perform the action of emitting the voice to the user U or the like as the action that acts on the emotion of the user U.

Furthermore, it is considered that, for example, a computer installed at a seat of an airplane is used as a device associated with the user U in the emotion inference system 1. Specifically, the computer installed at the seat of the airplane specifies the user U seated on the seat, performs conversation with the user U, and executes processing to the user U. In this case, the computer installed at the seat of the airplane infers the emotion of the user U on the basis of the voice of the user U. Additionally, as the action that acts on the emotion of the user U, position adjustment of the seat may be performed, or the voice may be emitted to the user U. Alternatively, a computer on which a microphone and a speaker are mounted may be installed in a fitting room of a store that sells clothing and the like, and this computer may be used as the device constituting the emotion inference system 1. This computer specifies the user U who uses the fitting room, performs conversation with the user U, and executes processing to the user U in the same manner as in the computer installed at the seat of the airplane. In this case, the computer installed in the fitting room infers the emotion of the user U on the basis of the voice of the user U. Furthermore, an action of emitting voice to the user U may be performed as the action that acts on the emotion of the user U.

Each device transmits the data used in inferring the emotion of the user U to the server 3 via the communication network 2. For example, when the user U uses each device, data obtained from the history of the operation performed to the device by the user U, or data obtained from contents or the like of conversation in voice which is performed between the user U and each device is collected and transmitted to the server 3. These pieces of data constitute the big data 21. The server 3 analyzes the big data 21. Furthermore, the big data 21 may be accumulated in the server 3.

The big data 21 is data collected by the respective devices of the emotion inference system 1 as described above. For example, the server 3 temporarily or continuously stores the big data 21. In the big data 21, the data (information) collected by each device is associated with information indicative of a category of the device that collects the information or unique identification information (ID or the like) given to the device, and is included. The category of the device may be set on the basis of an attribute of the device included in the emotion inference system 1. For example, household or living appliances, daily necessities, and the vehicle as a target of a driving operation are distinguished and set. Furthermore, the devices may be more finely categorized on the basis of a product use application, type, or common name.

The server 3 collects and accumulates the big data 21, and the individual personality 22 is configured on the basis of the big data 21. In the server 3, the individual personality 22 that is the artificial intelligence executes learning based on the big data 21 collected by the device associated with the user U. The individual personality 22 highly learns the emotion of the user U, and an algorithm to infer the emotion especially of the user U with high precision can be acquired. Furthermore, in the server 3, the concierge personality 23 that is the artificial intelligence may perform the learning based on the big data 21. In the emotion inference system 1, the concierge personality 23 can be used without allowing the concierge personality 23 to learn. Additionally, when it is useful to adapt the concierge personality 23 to the specific user U, the concierge personality 23 may perform the learning based on the big data 21.

The respective devices of the motorcycle 4, the automobile 11, the rice cooker 12, the vacuum cleaner 13, the television receiver 14, and the refrigerator 15 download and execute the program and/or data which constitute the individual personality 22, via the communication network 2. In consequence, the individual personality 22 can infer the emotion of the user U with high precision in each of the motorcycle 4, the automobile 11, the rice cooker 12, the vacuum cleaner 13, the television receiver 14, and the refrigerator 15. Furthermore, each device of the emotion inference system 1 downloads and executes a program and/or data that constitute the concierge personality 23, via the communication network 2.

The big data 21 includes data indicative of the emotion of the user U which is inferred by each device of the emotion inference system 1. This data may be a result obtained at a point of time when each device performs processing of inferring the emotion of the user U by the individual personality 22, or may be data of a history of inference of the emotion of the user U. Each of the plurality of devices transmits the history of inference of the emotion of the user U to the server 3, so that the server 3 can acquire, as the big data 21, the information on the emotion of the user U which is inferred at various times. Since this information is shared by the respective devices of the emotion inference system 1, each device can acquire data concerning the emotion of the user while the device is not used.

Each device of the emotion inference system 1 transmits data concerning a future schedule of the user U as the big data 21 to the server 3. That is, the big data 21 includes the data concerning the future schedule of the user U which is acquired by each device. Each device acquires the data concerning the future schedule of the user U, when the user U performs an input operation with a switch or a key or a voice input in each device. For example, in a case where the user U tells in voice a date to go on a trip and a trip destination to the rice cooker 12, the rice cooker 12 recognizes information of the trip destination and date by voice recognition. In this case, the rice cooker 12 transmits the information of the trip destination and date as the schedule of the user U to the server 3. This information is shared by each device of the emotion inference system 1 via the server 3 as described later. Alternatively, the server 3 or the other device of the emotion inference system 1 may acquire data concerning a schedule from the other communicably connected computer via the communication network 2.

Furthermore, each device of the emotion inference system 1 includes data input by the input operation with the switch or the key or the voice input by the user U, in addition to the future schedule of the user U. In the present embodiment, as one example, a shopping list is acquired by each device and transmitted as the big data 21 to the server 3.

The big data 21 may not only be utilized in the learning by the individual personality 22 but be also downloaded as a learning result of the individual personality 22 from the server 3 by each device.

In the emotion inference system 1, each device of the motorcycle 4, the automobile 11, the rice cooker 12, the vacuum cleaner 13, the television receiver 14, and the refrigerator 15 can detect or infer the emotion of the user U by utilizing the individual personality 22 that performs the learning based on the big data 21 including the data acquired by the other device. Then, each device can perform an action that acts on the emotion of the user U by utilizing the concierge personality 23 that performs the learning based on the big data 21.

For example, as shown in FIG. 1, the automobile 11 emits conversation voices 110, 111, 112, and 113 to the user U. The conversation voice 110 is a voice message to tell the user U playing of favorite music of the user U. The conversation voice 111 is a voice to tell the user U that a seat position of the automobile 11 and setting of a travelling operation to be executed by the automobile 11 in response to a driving operation are adapted to preference of the user U. The conversation voice 112 is a conversation voice to the user U which converses about the body weight of the user U on the basis of a weight detected by the weight sensor provided in the automobile 11. The conversation voice 113 is a voice that introduces tourist attractions in the vicinity or famous souvenirs in a case where the user U makes a trip by the automobile 11.

Furthermore, for example, the rice cooker 12 can emit a conversation voice 121 that converses about a destination to which the user U will go out on the basis of the future schedule of the user U which is included in the big data 21. Additionally, for example, the vacuum cleaner 13 can emit a conversation voice 131 calling on the user U to take measures of hay fever allergy on the basis of data indicative of that the user U has the hay fever allergy. The television receiver 14 can emit a conversation voice 141 that introduces a television program concerned with the previous activity of the user U on the basis of the future schedule of the user U and a record of contents of the conversation between the motorcycle 4 and the user U. The refrigerator 15 can emit a conversation voice 151 that prompts the user U to have coffee on the basis of the user's previous activity, specifically a history of use of the television receiver 14.

Each device of the emotion inference system 1 can not only unilaterally emit the voice to the user U but also make an interactive conversation in voice with the user U. This conversation in voice is achieved when the above computer provided in each device executes the concierge personality 23 and processes the data. These conversations may be so-called chatting.

Description will be made as to a configuration of each part of the emotion inference system 1.

FIG. 3 is a function block diagram of the server 3.

As shown in FIG. 3, the server 3 includes a server side control unit 31, a personality DB 34, a certification information storage unit 36, and a communication unit 38.

The communication unit 38 is connected to the communication network 2 by wire or wirelessly, and transmits and receives data via the communication network 2 in accordance with control of the server side control unit 31.

The server side control unit 31 is the control unit that controls each part of the server 3, and is configured on the basis of cooperation of a processor and a program to be executed by the processor. The server side control unit 31 is connected to the personality DB 34 and the certification information storage unit 36.

The server side control unit 31 is a processor that executes the program, and can be also called the processor 31. The processor 31 can use an integrated circuit, a microcontroller, a microcomputer, a programmable logic controller, an integrated circuit for a specific use application, or another programmable circuit. For example, the processor can include a central processing unit (CPU), a micro processing unit (MPU), the microcomputer, or another computation processing unit. The processor 31 may be an integrated chip (e.g., a so-called system-on-a-chip (SoC) device) in which a read only memory (ROM) and a random access memory (RAM) are integrated. The personality DB 34 is a storage device as an entity that stores data, and can be also called the storage device 34. Examples of the storage device 34 include a storage device in which a magnetic recording medium such as a hard disk drive (HDD) is used, and a storage device in which a semiconductor storage element such as a solid state drive (SSD), flash ROM, or static RAM (SRAM) is used. The certification information storage unit 36 may be configured by using a part of a storage region of the storage device 34. Separately from the storage device 34, the storage device 36 may be provided and may be configured as the certification information storage unit 36. In this case, a specific configuration of the storage device 36 can be similar to the storage device 34. The processor 31 executes the program stored in the storage device 34, and processes the data stored in the storage device 34, thereby achieving various functions of the server side control unit 31.

The server side control unit 31 includes an individual personality executing section 32, a personality forming section 311, a personality transfer section 312, a certification processing section 313, and a concierge personality forming section 314.

The personality DB 34 is a database including data concerning the individual personality 22 and the concierge personality 23. The personality DB 34 includes an individual personality 342, a base personality 343, activity schedule data 344, emotion detection history data 345, an emotion detection DB 346, a conversation DB 347, a corresponding action table 348, and a concierge personality 349. The individual personality 22 and the concierge personality 23 of FIG. 1 schematically show the individual personality 22 and the concierge personality 23 which are executed by the respective devices of the emotion inference system 1. These entities are the individual personality 342 and the concierge personality 349 in the server 3.

The certification information storage unit 36 stores certification information 361 that is information for certification.

The personality forming section 311 constitutes the individual personality 342 on the basis of the big data 21 (FIG. 1). The personality forming section 311 forms the individual personality 342, and stores the individual personality 342 in the personality DB 34. As described above, the individual personality 342 is a computer executable program.

In the emotion inference system 1, the individual personality 342 for a general purpose or in an initial state is stored in the personality DB 34 in a state before the big data 21 is collected.

The personality forming section 311 acquires the big data 21 transmitted from each device of the emotion inference system 1 via the communication unit 38. The personality forming section 311 extracts, from the big data 21, the data concerning the future schedule of the user U to generate the activity schedule data 344, and stores the activity schedule data 344 in the personality DB 34. The personality forming section 311 extracts, from the big data 21, an inference result of the emotion of the user U which is inferred by each device to generate the emotion detection history data 345, and stores the emotion detection history data 345 in the personality DB 34. The personality forming section 311 updates the activity schedule data 344 and the emotion detection history data 345, when the activity schedule data 344 and the emotion detection history data 345 are already stored in the personality DB 34.

The personality forming section 311 executes the learning of a target of the big data 21 by a learning function of the individual personality 342 stored in the personality DB 34. Through this learning, the individual personality 342 acquires an algorithm to infer the emotion of the user U. That is, the machine learning based on the big data 21 is performed, so that the emotion inference algorithm possessed by the individual personality 342 in the initial state is improved or modified to an algorithm directed for a purpose of inferring the emotion of the specific user U. There are not any restrictions on a specific aspect of the improvement or the modification of the algorithm, and change of the program itself may be included, or change of a parameter that prescribes the operation of the program may be included. Consequently, the individual personality 342 acquires the algorithm so that the emotion of the user U is inferred with high precision and the emotion or movement of the emotion is generated so as to imitate the emotion of the user U.

The personality forming section 311 reads the individual personality 342 from the personality DB 34 to execute the personality, causes the above learning to be executed on the basis of the function of the program of the individual personality 342, and stores the learned individual personality 342 in the personality DB 34. Note that in the personality forming section 311, the learning of the individual personality 342 may be performed by executing a program that has a function of updating the individual personality 342 and that is separate from the individual personality 342.

The server 3 forms the concierge personality 349. In the simplest method, the concierge personality 349 for a general purpose or in an initial state is stored in the personality DB 34 before the big data 21 is collected. The concierge personality 349 stored in the personality DB 34 may be utilized in the emotion inference system 1. Alternatively, the personality forming section 311 reads the concierge personality 349 stored in the personality DB 34 to execute the personality, and causes the learning based on the big data 21 to be executed by the learning function of the concierge personality 349. The concierge personality 349 is a computer executable program. Through this learning, the concierge personality 349 acquires an algorithm that acts on the emotion of the individual personality 342. The concierge personality 349 controls the conversation or the device to act on and direct the emotion of the individual personality 342 in a specific direction or a tendency or toward a specific emotion. A purpose of an action to be executed by the concierge personality 349 is to induce the emotion of the user U in a targeted direction. The concierge personality 349 performs the machine learning based on the big data 21, which makes it possible to effectively act on the emotion of the specific user U, so that the emotion of the user U can be more securely induced in the targeted direction. Consequently, the concierge personality 349 performs the improvement and modification of the algorithm through the learning. There are not any restrictions on the specific aspect of the improvement or modification of the algorithm, and the change of the program itself may be included, or the change of the parameter that prescribes the operation of the program may be included. The personality forming section 311 updates the concierge personality 349 of the personality DB 34 every time the learning of the concierge personality 349 proceeds.

The personality transfer section 312 transmits a program including the individual personality 342 and the data via the communication unit 38 in response to a request, when any device that constitutes the emotion inference system 1 makes the request for transfer of the individual personality 342 that is the individual personality 22. In the present embodiment, the personality transfer section 312 transmits the personality DB 34 including the other data for use in a case where the individual personality 342 operates, in addition to the individual personality 342, via the communication unit 38.

The certification processing section 313 executes certification processing, when the server 3 is accessed by the other device via the communication network 2. The certification processing section 313 compares information transmitted by the device that has accessed the server 3 with the certification information 361 stored in the certification information storage unit 36, thereby executing certification. When the respective devices of the motorcycle 4, the automobile 11, the rice cooker 12, the vacuum cleaner 13, the television receiver 14, and the refrigerator 15 shown in FIG. 1 access the server 3 via the communication network 2, the devices transmit identification information such as a user ID corresponding to the user U and certification information such as a password. The identification information and the certification information of the user U are unique to the user U. The certification processing section 313 specifies the user U who uses this device, when executing the certification of the device that has accessed the server 3. For example, when the emotion inference system 1 executes the above described function to a plurality of users U, the server 3 has the personality DB 34 for each user U. Consequently, the certification processing section 313 specifies the user U who uses the device to be certified when executing the certification, and the server side control unit 31 processes the personality DB 34 concerning the user U specified by the certification when succeeding in the certification.

When the certification by the certification processing section 313 is successful, the personality transfer section 312 transmits the personality DB 34 via the communication unit 38. The personality transfer section 312 may select the data or program to be transmitted from the personality DB 34 in accordance with a category or the like of the device certified by the certification processing section 313.

The individual personality executing section 32 executes the individual personality 342. When there is a need to execute the individual personality 342 that is the program including the algorithm of the artificial intelligence in the server 3, this processing is executed by the individual personality executing section 32.

The individual personality 342 is the artificial intelligence that imitates the emotion of the user U or the change of the emotion as described above, and specifically includes a program to execute the algorithm, and data to be processed by the above program. The individual personality 342 has an algorithm corresponding to a learning function of performing learning concerning the user U on the basis of the big data 21, an emotion detecting function of inferring (detecting) the emotion of the user U, a conversation executing function of performing conversation with the user U, or the like.

The base personality 343 includes a program and data concerning the base personality that is a virtual personality formed according to the algorithm of the individual personality 342. The base personality will be described later.

The activity schedule data 344 includes the data concerning the future schedule of the user U, and is configured on the basis of, for example, the data extracted from the big data 21. The activity schedule data 344 is configured on the basis of the information extracted, by the personality forming section 311, from the big data 21 transmitted by each device constituting the emotion inference system 1. The personality forming section 311 may receive the data concerning the future schedule of the user U from an external server (not shown) connected via the communication network 2, and may include the data in the activity schedule data 344.

The emotion detection history data 345 is data including a history of detection of the emotion of the user U in the respective devices of the motorcycle 4, the automobile 11, the rice cooker 12, the vacuum cleaner 13, the television receiver 14, and the refrigerator 15. Here, the emotion of the user U may be an emotion of the individual personality 342 which imitates the emotion of the user U. In this case, the emotion detection history data 345 may include information on a history of an emotion of the individual personality 342.

The activity schedule data 344 and the emotion detection history data 345 include the activity schedule data 344 and the emotion detection history data 345 transmitted by the respective devices of the emotion inference system 1, and may include the other data extracted from the big data 21 by the personality forming section 311.

The emotion detection DB 346 includes various pieces of data which are utilizable as detection values concerned with the emotion of the user U. For example, the emotion detection DB 346 may include data such as rhythm, sound quality, and vocal sound obtained by analyzing the voice of the user U detected by the microphone, and a parameter indicative of the emotion of the user U. Furthermore, the emotion detection DB 346 may include data concerning a captured image obtained by imaging a face of the user U with a camera. Specifically, data indicative of a feature of the face image of the user U which is extracted from the captured image and data indicative of the emotion of the user U may be included.

The data included in the emotion detection DB 346 is for use, for example, in a case where the individual personality 342 detects the emotion of the user U. The individual personality 342 refers to the data of the emotion detection DB 346, when inferring (detecting) the emotion of the user U from data obtained by collecting the voice of the user U or the captured image of the face of the user U according to the algorithm for the detection of the emotion. Furthermore, the individual personality 342 can refer to the data included in the emotion detection DB 346 in order to imitate the emotion of the user U. Additionally, the concierge personality 349 may refer to the data of the emotion detection DB 346, when performing processing to cope with the emotion of the user U.

Furthermore, the individual personality 342 may utilize the data included in the emotion detection DB 346 during the machine learning. This machine learning is so-called supervised learning performed by using training data in which a voice, facial expression, and action of a companion are associated with an emotion of the companion. As the training data, a large number of pieces of data are usable in which, for example, the rhythm, sound quality, and vocal sound of the voice, the facial expression and an activity (a gesture or the driving operation) differ in a wide variety. Additionally, the emotions of the training data are classified into "joy", "anger", "sadness", "pleasure", "impatience", "insecurity", and "neutrality", together with degrees of the emotions. Through such a machine learning, an algorithm is obtained to classify the emotion of the companion together with the degree of the emotion on the basis of the voice, facial expression, and activity. Furthermore, as the training data, a detection result of the emotion of the user U detected by the device constituting the emotion inference system 1 in the past and the information on the user U may be used.

The conversation DB 347 includes data for use in a case where the concierge personality 349 executes the conversation with the user U by utilizing the algorithm for the conversation. Specifically, there are included data of a word dictionary, a pronunciation dictionary, a voice dictionary, and the like for use in a case where the concierge personality 349 synthesizes a conversational sentence.

Furthermore, the conversation DB 347 may include data for use in a case where the individual personality 342 analyzes the voice of the user U.

The corresponding action table 348 is data in the form of a table that determines an action to be executed in response to the emotion of the user U. The corresponding action table 348 includes data concerning the emotion of the user U, and data to determine the action that acts on the user U to suppress or calm the emotion of the user U.

An action to be performed to the user U by each device of the emotion inference system 1 varies with the type of device. In the server 3, the personality DB 34 may store the corresponding action table 348 for each category of the device or for each device. For example, the personality DB 34 may store a plurality of corresponding action tables 348. Alternatively, the corresponding action table 348 stored in the server 3 may include a table corresponding to each of a plurality of categories or each of a plurality of devices. In this case, one corresponding action table 348 may be configured to include the data concerning a plurality of devices.

The concierge personality 349 includes artificial intelligence that copes with the emotion of the user U and that performs control to direct the emotion of the user U in a predetermined direction, and specifically includes a program to execute the algorithm, and data to be processed by the above program.

FIG. 4 is a function block diagram showing a configuration of a control system of the motorcycle 4.

The motorcycle 4 will be described as one example of the device associated with the user U in the emotion inference system 1.

The motorcycle 4 may be a saddle bike or a scooter. The motorcycle 4 includes a sensor unit 43 including various sensor concerned with travelling, and an action unit 44 that executes various operations concerned with the travelling. Furthermore, the motorcycle 4 includes an ECU 41 that controls the sensor unit 43 and the action unit 44. The respective units of the ECU 41, the sensor unit 43, and the action unit 44 of the present embodiment are not different from general motorcycles, and detailed configurations of the ECU 41, the sensor unit 43, and the action unit 44 are merely illustrations.

The sensor unit 43 includes an illumination sensor 431, a switch 432, a throttle sensor 433, a steering angle sensor 434, a brake sensor 435, a temperature sensor 436, and a vehicle speed sensor 437. The illumination sensor 431 detects ambient brightness of the motorcycle 4. The switch 432 is any type of switch provided in the motorcycle 4, and includes, for example, a turn signal switch, a headlight switch, a cell starter switch, and the like. The throttle sensor 433 detects an operation amount of a throttle installed at a handlebar (not shown) of the motorcycle 4. The steering angle sensor 434 detects an operation amount of a handlebar operation of the motorcycle 4. The brake sensor 435 detects an operation amount of a brake lever of the motorcycle 4. When the motorcycle 4 includes a foot brake to be operated with a foot of the user U, the brake sensor 435 may detect an operation amount of the foot brake. The temperature sensor 436 detects a temperature of an engine of the motorcycle 4 and/or a temperature of a drive system of a transmission or the like of the motorcycle 4. For example, when the engine mounted on the motorcycle 4 is a water cooling engine, the temperature sensor 436 may detect a water temperature of cooling water. The vehicle speed sensor 437 detects a traveling speed of the motorcycle 4.

Except for the switch 432, the respective sensors constituting the sensor unit 43 execute the detection in accordance with the control of the ECU 41, and output detection values to the ECU 41. Furthermore, the ECU 41 can usually detect a switched state of the switch 432.

The action unit 44 includes a throttle device 441, a fuel injection device 442, an ignition device 443, a transmission 444, a brake drive device 445, a lighting device 446, a suspension adjustment section 447, and a meter panel 448.

The throttle device 441 adjusts an opening degree of a throttle valve (not shown) of the motorcycle 4 in accordance with the control of the ECU 41. The fuel injection device 442 injects fuel in accordance with the control of the ECU 41. The fuel injection device 442 provided in the motorcycle 4 may be a port injection device or a direct injection device, and there are not any special restrictions on a number of injection nozzles, or the like. When the fuel injection device 442 is the port injection device, the device injects the fuel in accordance with the opening degree of the throttle valve. Furthermore, an amount of the fuel to be injected by the fuel injection device 442 can be controlled by the ECU 41.

The ignition device 443 includes a spark plug of the engine of the motorcycle 4, and a circuit that supplies a voltage to the spark plug. Thus, the ECU 41 controls the ignition device 443, so that an ignition timing in each cylinder of the engine of the motorcycle 4 can be controlled. The transmission 444 is an automatic transmission coupled to the engine, and executes transmission in accordance with the control of the ECU 41. The transmission 444 is, for example, the automatic transmission (AT), a belt AT, a continuously variable transmission (CVT), a dual clutch transmission (DCT), or the like. The brake drive device 445 is a brake device disposed in each of a front wheel and a rear wheel of the motorcycle 4, and mechanically performs braking in response to an operation of the brake lever or the foot brake. The brake drive device 445 has a brake booster that assists an operation force of the brake lever or the foot brake to increase a braking force, and this brake booster can be controlled by the ECU 41. The brake drive device 445 may be configured to brake at a timing and with the braking force as determined by the ECU 41 in response to the operation of the brake lever or the foot brake. The lighting device 446 includes a headlamp, a turn signal lamp, a brake lamp, and another marker lamp of the motorcycle 4. The lighting device 446 controls lighting and extinguishing of at least parts of the lamps in accordance with the control of the ECU 41.

The suspension adjustment section 447 adjusts a suspension device (not shown) interposed between a tire and a vehicle body frame in the motorcycle 4. For example, when the motorcycle 4 includes an active suspension device, the suspension adjustment section 447 adjusts the vehicle height of the motorcycle 4, a damping force of a damper, or the like in accordance with the control of the ECU 41. The meter panel 448 displays a vehicle speed, an engine speed, a traveling distance, lighting states of the lamps, a residual amount of the fuel, and the like of the motorcycle 4. The meter panel 448 has a backlight to enhance visibility in a dark place or at night, and in the present embodiment, an emission color of the backlight can be changed under the control of the ECU 41.

The ECU 41 includes a detection control section 411, a throttle control section 412, a fuel injection control section 413, an ignition control section 414, a brake control section 415, a suspension control section 416, a lamp lighting control section 417, and a display control section 418.

The ECU 41 is a processor that executes the program, and can be also called the processor 41. The processor 41 can use an integrated circuit, a microcontroller, a microcomputer, a programmable logic controller, an integrated circuit for a specific use application, or another programmable circuit. For example, the processor can include a CPU, a MPU, the microcomputer, or another computation processing unit. Alternatively, the processor 41 may be an integrated chip (e.g., a so-called SoC device) in which ROM and RAM are integrated. The ECU 41 executes the program stored in the unshown ROM, thereby achieving functions of the detection control section 411, the throttle control section 412, the fuel injection control section 413, the ignition control section 414, the brake control section 415, the suspension control section 416, the lamp lighting control section 417, and the display control section 418.

The detection control section 411 acquires a detection value of each type of sensor included in the sensor unit 43 and a state of the switch 432. The throttle control section 412 operates the throttle device 441 on the basis of the detection value detected by the detection control section 411 and the like. The fuel injection control section 413 controls a fuel injection timing or injection amount by the fuel injection device 442 on the basis of, for example, the detection value detected by the detection control section 411. The ignition control section 414 controls the ignition device 443 on the basis of the detection value detected by the detection control section 411 and the like, and ignites the spark plug at an appropriate timing. The brake control section 415 controls the brake drive device 445, thereby controlling an operation of the brake booster. The suspension control section 416 controls the suspension adjustment section 447 to perform the adjustment of the vehicle height of the motorcycle 4, setting such as suspension setting, and the like. The lamp lighting control section 417 controls lighting and extinguishing of each lamp constituting the lighting device 446 in accordance with the switched state of the switch 432. The display control section 418 performs switching of the lighting and extinguishing of the backlight of the meter panel 448, and changing of the emission color of the backlight.

The motorcycle 4 can travel in response to the operation of the user U by the functions of the ECU 41, the sensor unit 43, and the action unit 44. It can be considered that these units constitute a minimum configuration required for the traveling by the motorcycle 4.

Furthermore, the motorcycle 4 includes a device side control unit 46, a communication unit 47, a personality DB 48, and an external sensor 49. The device side control unit 46 is a function unit to execute an individual personality 482 that includes artificial intelligence, and is configured on the basis of cooperation of a processor and a program executed by the processor. The device side control unit 46 is connected to the personality DB 48 and the external sensor 49.

The device side control unit 46 is a processor that executes a program, and can be also called the processor 46. The processor 46 can use an integrated circuit, a microcontroller, a microcomputer, a programmable logic controller, an integrated circuit for a specific use application, or another programmable circuit. For example, the processor can include a CPU, a MPU, the microcomputer, or another computation processing unit. Alternatively, the processor 46 may be an integrated chip (e.g., a so-called SoC device) in which ROM and RAM are integrated. Additionally, the personality DB 48 is a storage device as an entity that stores data, and can be also called the storage device 48. Examples of the storage device 48 include a storage device in which a magnetic recording medium such as an HDD is used, and a storage device in which a semiconductor storage element such as an SSD, flash ROM or SRAM is used.

The communication unit 47 is connected to the communication network 2, and executes communication with the server 3 (FIG. 1) via the communication network 2. The communication unit 47 transmits data output by the device side control unit 46 to the server 3, and outputs data received from the server 3 to the device side control unit 46. The external sensor 49 includes a headset 491, a camera 494, a G sensor 495, a GPS receiving section 496, and a wireless communicating section 497. The headset 491 is provided on a helmet attached to the user U, and has a microphone 492 and a speaker 493. The microphone 492 collects the voice emitted by the user U to output a voice signal to the device side control unit 46. The speaker 493 may be an earphone to be attached to an ear of the user U, and outputs the voice in accordance with the control of the device side control unit 46. Here, an analog/digital (A/D) converter that converts an analog voice signal to digital data may be disposed between the headset 491 and the device side control unit 46, or the headset 491 may include the A/D converter.

The camera 494 includes an image sensor such as a charge coupled device (CCD) or a complementary metal oxide semiconductor (CMOS), images an imaging range including the face of the user U, and outputs captured image data to the device side control unit 46. The G sensor 495 is a sensor that detects an acceleration, and outputs a detection value to the device side control unit 46. The G sensor 495 may be a uniaxial sensor that detects an acceleration G in a uniaxial sensor, or may be a biaxial or tri-axial sensor. Alternatively, the G sensor 495 may be an integrated motion sensor unit combined with an angular velocity sensor or the like.

The GPS receiving section 496 includes an antenna (not shown) that receives a GPS signal, measures a current position of the motorcycle 4, and outputs a measurement result to the device side control unit 46.

The wireless communicating section 497 performs short-range communication by utilizing at least a short-range wireless communication protocol. The short-range wireless communication is wireless communication in which a communication area is from at least several ten centimeters to several meters or more. Examples of the short-range wireless communication include Bluetooth (registered trademark), IrDA (registered trademark), radio frequency identification (RFID), and IEEE 802.11 (so-called wireless LAN). The wireless communicating section 497 executes wireless communication with, for example, a smartphone, a wireless microphone, or another device that is possessed for use by the user U.

Various pieces of data stored in the personality DB 48 are the data stored in the personality DB 34 possessed by the server 3 (FIG. 2). The device side control unit 46 accesses the server 3 via the communication unit 47, and stores data downloaded after the certification processing in the personality DB 48.

The individual personality 482 includes the artificial intelligence that imitates the emotion of the user U or the change of the emotion as described above, and specifically includes a program to execute the algorithm, and data to be processed by the above program. The individual personality 482 is, for example, the individual personality 342 that has performed the learning in the server 3 and is downloaded to the device side control unit 46.

A base personality 483 includes a program and data concerning the base personality that is a virtual personality formed according to the algorithm of the individual personality 482.

The individual personality 482 is a virtual personality that has an emotion tendency similar to the user U or imitates the emotion tendency of the user U. The individual personality 482 copes with an external factor, simulates an emotion change of the user U, and generates an emotion that imitates the emotion of the user U. Here, the individual personality 482 may imitate the emotion of the user U on the basis of both the external factor and the emotion of the user U which is generated or changed in accordance with this external factor.

An individuality is reflected in a human emotion, and a certain person may have, for example, a tendency to recall a particular emotion. There is an individual variation in a character tendency, an emotion tendency, or characteristic of such a user U, and, for example, there are a person who is easy to recall an emotion of anger and a person who normally seems to have a state of feeling a little irritation. The base personality 483 additionally takes the emotion tendency of the user U into consideration, and shows an emotion held by the user U in a usual state. The base personality 483 may be a program having an algorithm that generates or changes the emotion, or AI, but may be a reference value indicative of a kind and a degree of the emotion. The user U in the usual state is a virtual personality specified on the basis of the big data 21 collected by the respective devices constituting the emotion inference system 1. To be brief, any emotion to be held by "any usual user U" can be obtained from the emotion of the base personality 483.

The base personality 483 may be, for example, formed by the server 3 and transmitted (distributed) to the respective devices of the motorcycle 4, the automobile 11, the rice cooker 12, the vacuum cleaner 13, the television receiver 14, and the refrigerator 15. In the present embodiment, the base personality is formed by at least any one of the respective devices of the motorcycle 4, the automobile 11, the rice cooker 12, the vacuum cleaner 13, the television receiver 14, and the refrigerator 15. According to the present embodiment, in the motorcycle 4, the device side control unit 46 forms the base personality 483 as described later.

Activity schedule data 484 (an activity schedule table) is data similar to the activity schedule data 344 stored in the personality DB 34, and includes the data concerning the future schedule of the user U. The motorcycle 4 downloads the activity schedule data 344 from the server 3 and stores the data in the personality DB 48. Consequently, the device side control unit 46 can refer to the latest activity schedule data 484.

Emotion detection history data 485 (an emotion accumulation unit) is data of a history of inference and detection of the emotion of the user U, and is downloaded from the server 3 by the device side control unit 46. The emotion detection history data 485 includes data of a history of inference of the emotion of the user U by the device side control unit 46 in the motorcycle 4. Furthermore, the data includes a history of inference of the emotion of the user U by the other device (the automobile 11, the rice cooker 12, the vacuum cleaner 13, the television receiver 14, or the refrigerator 15) of the emotion inference system 1.

An emotion detection DB 486 includes various pieces of data which are utilizable as detection values concerned with the emotion of the user U. The emotion detection DB 486 includes data similar to the emotion detection DB 346 stored in the personality DB 34. The emotion detection DB 486 may be downloaded from the server 3 by the device side control unit 46 and stored in the personality DB 48.

A conversation DB 487 includes data for use in a case where the device side control unit 46 utilizes the algorithm for the conversation to execute the conversation with the user U, and includes, for example, data similar to the conversation DB 347 stored in the personality DB 34.

A corresponding action table 488 is data in the form of a table that determines an action to be executed in response to the emotion of the user U. The corresponding action table 488 includes data concerning the emotion of the user U, and data to determine the action that acts on the user U to suppress or calm the emotion of the user U. In particular, the corresponding action table 488 is the table that determines an action to be executed in response to the emotion of the user U by the motorcycle 4, and may not include data concerning an action to be executed by the other device, such as the automobile 11 or the rice cooker 12. For example, the device side control unit 46 may download only the data concerned with the action of the motorcycle 4 from the corresponding action table 348 stored in the personality DB 34, and may store the data as the corresponding action table 488.

A concierge personality 489 includes the artificial intelligence that copes with the emotion of the user U and that performs control to direct the emotion of the user U in a predetermined direction, and specifically includes a program to execute the algorithm, and data to be processed by the above program.

The device side control unit 46 executes the individual personality 482 stored in the personality DB 48, and the concierge personality 489, thereby achieving various functions of the artificial intelligence. The device side control unit 46 has a communication control section 461, an external sensor control section 462, a vehicle sensor control section 463, an emotion detecting section 464, a traveling state adjustment section 465, a conversation executing section 466, an output control section 467, a base personality forming section 468, an emotion change cause inferring section 469, and an action control section 470. Among these sections, at least the emotion detecting section 464, the base personality forming section 468, and the emotion change cause inferring section 469 are functions achieved by executing the individual personality 482. Furthermore, the action control section 470 is a function achieved by executing the concierge personality 489. The traveling state adjustment section 465 and the conversation executing section 466 are functions achieved in association with the concierge personality 489. The other functions may be configured by executing a program different from the individual personality 482 by a processor for use in the device side control unit 46.

The communication control section 461 controls the communication unit 47 to execute the data communication via the communication network 2. The communication control section 461 executes an operation of transmitting information for certification to the server 3, an operation of downloading the data included in the personality DB 34 from the server 3, and the like. Alternatively, the communication control section 461 may control the wireless communicating section 497 to execute data communication with each device.

The external sensor control section 462 controls each part of the external sensor 49 to acquire a detection value. Specifically, the external sensor control section 462 acquires detection values or detection results of the microphone 492, the camera 494, the G sensor 495 and the GPS receiving section 496.

The vehicle sensor control section 463 acquires, from the ECU 41, the detection value of each sensor included in the sensor unit 43 under the control of the ECU 41. Consequently, the artificial intelligence executed by the device side control unit 46 can utilize the detection value detected by the sensor unit 43.

The emotion detecting section 464 (a driving tendency judging section) infers the emotion of the user U. The emotion detecting section 464 is a function of the above described individual personality 482. The emotion detecting section 464 detects the emotion of the user U from the voice of the user U which is collected with the microphone 492 and the captured image of the camera 494. Furthermore, the emotion detecting section 464 acquires data concerning the emotion of the user U detected in the past or the data concerning the immediately previously detected emotion of the user U with reference to the emotion detection history data 485, and can use the data in emotion detection. In this case, data concerning the emotion of the user U detected by the other device can be also used. Additionally, the emotion of the user U can be detected by using the emotion detection history data 485, referring to the activity schedule data 484 and additionally referring to the future schedule of the user U. In the present embodiment, it has been described that the individual personality 482 has the function of the emotion detecting section 464, but the emotion detecting section 464 may be a function achieved by the concierge personality 489.

The emotion detecting section 464 uses the algorithm obtained by the machine learning to infer the emotion of the user U. This machine learning is so-called supervised learning performed by using the training data as described above. The emotion detecting section 464 receives the input of the voice, facial expression, and activity of the user U, and outputs the classification of the emotion of the user U and the degree of the emotion according to the above algorithm. Note that the classification of the emotion is merely illustration, and may be appropriately changed as required. In the emotion detecting section 464, an existing optional emotion recognition technology can be used in place of the inference in which the algorithm obtained by the machine learning is used.

Here, the emotion detecting section 464 is not limited to a section that detects the emotion directly from the detection result of the external sensor 49 which is acquired by the external sensor control section 462, the detection result of the sensor unit 43 which is acquired by the vehicle sensor control section 463, and the data of the history included in the emotion detection history data 485. For example, the emotion detecting section 464 may infer or detect the emotion of the user U by simulating (imitating) the emotion of the user U or the movement of the emotion on the basis of the detection results of the sensor unit 43 and the external sensor 49 and the data of the emotion detection history data 485.

Then, the emotion detecting section 464 further adds the base personality 483 to the result obtained by inferring the emotion of the user U, to detect the emotion of the user U. The emotion detecting section 464 compares the inferred emotion of the user U with the emotion of the base personality 483, and specifies the emotion of the user U. The result obtained by comparing the emotion of the user U with the emotion of the base personality 483 by the emotion detecting section 464 is called an emotion attribute.

Furthermore, the emotion detecting section 464 of the present embodiment uses a mode of an operation when the user U drives the motorcycle 4, as the parameter to detect the emotion of the user U.

Figure 6:
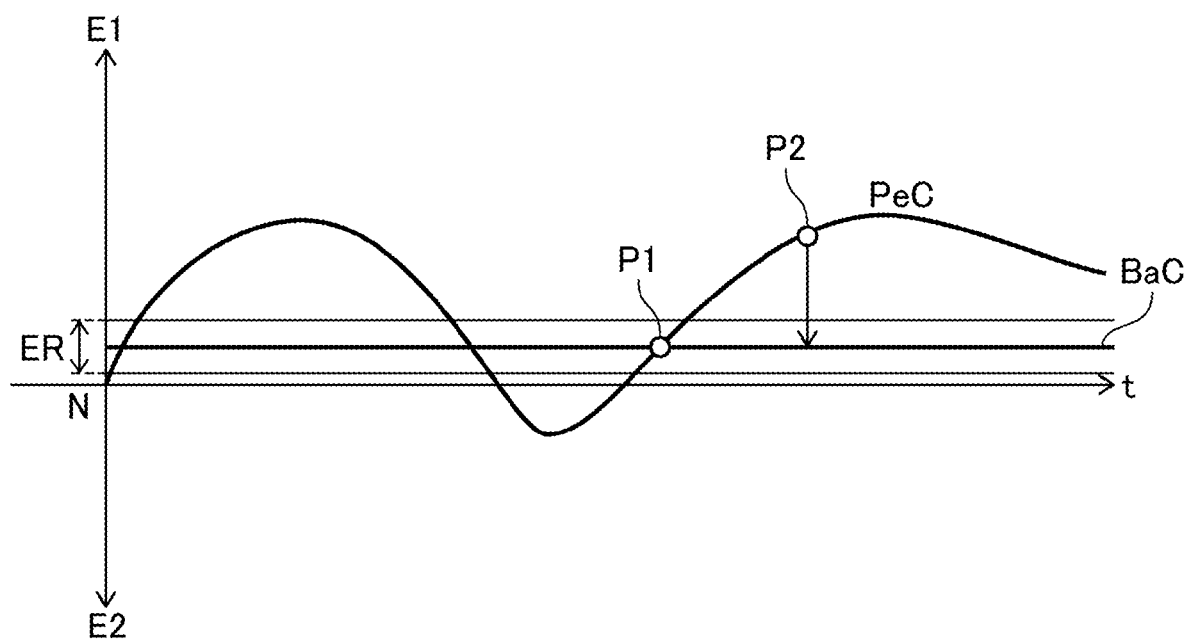
FIG. 6 is an explanatory diagram showing a relation between an individual personality and a base personality.

FIG. 5 is a schematic diagram showing a configuration example of emotion detection setting data 401 to set a parameter for a case where the emotion detecting section 464 detects the emotion of the user U. The emotion detection setting data 401 is stored, for example, as one piece of data concerned with the individual personality 482 or the concierge personality 489, in the personality DB 48. Furthermore, FIG. 6 is an explanatory diagram showing a relation between the individual personality 482 and the base personality 483.

For example, it is assumed that the user U is a person or a character who often holds the emotion of "sadness". Such a user U holds the emotion of "sadness" on a daily basis, and the emotion is a usual state for the user U. So to speak, it can be considered that the emotion of the user U is not a state of being conscious of "sadness" and that the emotion is "calm". On the other hand, when the user U who extremely rarely holds the emotion of "sadness" holds the emotion of "sadness", this emotion is held on a non-daily basis and is a very unusual state for the user U himself/herself. Thus, importance of a case where "sadness" is detected as the emotion of the user U differs in accordance with a tendency or nature of the emotion of the user U.

The emotion detecting section 464 obtains the emotion held by a personality of the user U which can be obtained from the big data 21 with reference to the emotion of the base personality 483, and compares this emotion with the inferred emotion of the user U. Consequently, it is possible to infer and detect, with high precision, what kind of emotion is for the user U himself/herself.

In the emotion detection setting data 401 of FIG. 5, the voice, the throttle opening, the brake operation amount, a detection value of the G sensor 495, the captured image of the camera 494, and the like are set as the data acquired in a case where the emotion detecting section 464 detects the emotion of the user U, i.e., as the detection values. The voice is detected with the microphone 492. The emotion detecting section 464 utilizes conversation contents, a frequency or a number of times of monologues, monologue contents, and the like as parameters for the emotion detection with respect to the voice detected with the microphone 492. Furthermore, the throttle opening is the detection value of the throttle sensor 433, and the emotion detecting section 464 utilizes a change of the throttle opening as the parameter for the emotion detection. The brake operation amount is the detection value of the brake sensor 435. For example, when the user U holds the emotion of "anger", the operation of the throttle valve or brake becomes violent, and the detection values of the throttle sensor 433 and the brake sensor 435 steeply change. Furthermore, a behavior of a vehicle body of the motorcycle 4 becomes unstable, and therefore the change of the detection value of the GPS receiving section 496 becomes steep. Such a change can be utilized in detecting the emotion of the user U. The detection values and parameters that are set in the emotion detection setting data 401 can be utilized also in detecting the emotion of the base personality 483.

FIG. 6 shows the change of the emotion of the user U as a graph. In the graph of FIG. 6, an ordinate indicates an emotion axis, and an abscissa indicates elapse of time. The emotion of the ordinate may be any emotion, but as one example in FIG. 6, the axis of "anger" (emotion E1) to "calmness" (emotion E2) is shown. A point N on the ordinate is a neutral point indicative of a neutral state of the emotion. When the emotion of the user U is at the neutral point N, the emotion is neutralized in the comparison between "anger" and "calmness".

FIG. 6 shows the emotion of the base personality 483 with a curve BaC. The curve BaC of FIG. 6 seems to be a straight line, but may be a curved line. Furthermore, the emotion of the individual personality 482 is shown with a curve PeC. The individual personality 482 changes so as to imitate the emotion of the user U, and hence it can be considered that the curve PeC indicates (or simulates) the change of the emotion of the user U.

As is clear from the comparison between the curve BaC, and the ordinate and the abscissa, in the example of FIG. 6, the base personality 483 having the usual emotion of the user U is at a position biased to "anger" from the neutral point N. Consequently, at a point P1, the emotion of the individual personality 482 indicated by the curve PeC is at a position biased to "anger" from the neutral point N, and overlaps with the curve BaC. That is, at the point P1, the emotion of the individual personality 482 meets the base personality 483 that is "the usual emotion of the user U". In this case, the emotion is biased to "anger", but it can be considered that the user U is in a cool and steady state.

At a point P2 of FIG. 6, the curve PeC is at a position biased to "anger" more largely than the curve BaC. In this case, the action control section 470 executes an action of the motorcycle 4 to bring the emotion of the point P2 close to the emotion of the curve BaC. Specifically, the action control section 470 controls the traveling state adjustment section 465, the conversation executing section 466, and the output control section 467, thereby executing various operations.

Furthermore, at the point P2 of FIG. 6, there is a difference in an ordinate direction between the emotion of the individual personality 482 and the emotion of the base personality 483, and it can be considered that this difference is the emotion attribute.

The action control section 470 has a reference range ER as a reference to execute the action that brings the emotion of the individual personality 482 close to the emotion of the base personality 483. In the example of FIG. 6, the reference range ER is set so as to have a predetermined width in a plus direction and a minus direction from the emotion of the base personality 483 along the emotion axis. The width of the reference range ER in the plus direction and the width in the minus direction may be set independently respectively, or may be set so that the emotion of the base personality 483 is in the center. Furthermore, a size of the reference range ER may be set for each kind of emotion detected by the emotion detecting section 464. For example, the size can be set to a predetermined % in the plus direction and a predetermined % in the minus direction on the basis of the emotion of the base personality 483 along the emotion axis.

In a case where the emotion of the individual personality 482 deviates from the emotion of the base personality 483 in excess of the reference range ER, the action control section 470 judges that this case corresponds to a case where there are predetermined or more changes in the emotion of the individual personality 482. That is, it can be considered that the size of the reference range ER is a predetermined range as a reference in judging the change of the emotion of the individual personality 482.

The size of the reference range ER differs with each user U. For example, the size of the reference range ER is determined on the basis of a characteristic of the base personality 483 which indicates that emotional ups and downs and the emotion changes are small, large, or the like. The size of the reference range ER may be determined by, for example, the emotion detecting section 464 or the action control section 470. Thus, the reference range ER is set, so that the reference for the action control section 470 to execute the action becomes clear when the emotion detected by the emotion detecting section 464 is separated from the emotion of the base personality 483. Consequently, a frequency of actions that acts on the user U and are to be performed by the action control section 470 can be suppressed to an appropriate degree, and a situation where the section excessively interferes with the emotion of the user U can be avoided. In consequence, while the user U is not annoyed by the control of the action control section 470, the emotion of the user U can be effectively induced and quieted down, and the user U can comfortably and stably drive the motorcycle 4.

Returning to FIG. 4, the action control section 470 executes the action that acts on the emotion of the user U on the basis of the emotion of the user U which is detected by the emotion detecting section 464. The action control section 470 controls the traveling state adjustment section 465 to operate each section of the action unit 44. Furthermore, the action control section 470 controls the conversation executing section 466 to execute the conversation between the section and the user U. Additionally, the action control section 470 controls the output control section 467 to execute an operation differently from the traveling state adjustment section 465 and the conversation executing section 466. The operations to be executed by the traveling state adjustment section 465, the conversation executing section 466, and the output control section 467 under the control of the action control section 470 are set in the corresponding action table 488 described later.

The traveling state adjustment section 465 operates the action unit 44 according to the control of the action control section 470 as described later.

The conversation executing section 466 executes the conversation in voice with the user U in accordance with the control of the action control section 470. The conversation executing section 466 controls the microphone 492 and the speaker 493 according to the conversation algorithm the artificial intelligence has, to perform the conversation in voice. Here, the conversation executing section 466 may recognize the voice emitted by the user U, or select or construct a word or a sentence to be uttered to the user U, with reference to the conversation DB 487.

The output control section 467 executes the action other than the actions executed by the traveling state adjustment section 465 and the conversation executing section 466 in accordance with the control of the action control section 470.

The base personality forming section 468 forms the base personality 483.

The emotion change cause inferring section 469 infers a factor that leads to the change of the emotion in a case where the emotion of the user U detected by the emotion detecting section 464 significantly changes. The emotion detecting section 464 detects the emotion of the user U every set time or at a timing determined by an external factor. The emotion change cause inferring section 469 obtains a difference between the emotion of the user U detected by the emotion detecting section 464 and the emotion previously, especially immediately previously detected by the emotion detecting section 464 or the other device. Data concerning the emotion detected by the emotion detecting section 464 in the past and the emotion detected by the other device in the past are included in the emotion detection history data 485. The factors that change the emotion of the user U are variously present, and the emotion change cause inferring section 469 of the present embodiment searches for a schedule that becomes the factor for the emotion change from the data concerning the schedule of the user U which is included in the activity schedule data 484.

FIG. 7 is a schematic diagram showing a configuration example of the corresponding action table 488. FIG. 8 is a schematic diagram showing a configuration example of a corresponding action table 488*a*. The corresponding action table 488*a* constitutes a part of the corresponding action table 488 of FIG. 7.

As described above, an action to be executed by each device of the emotion inference system 1 in response to the emotion of the user U differs with each device. FIG. 7 and the corresponding action table 488*a* shown in FIG. 8 show an example of setting with respect to the action of the motorcycle 4. In the corresponding action table 488, the action to be executed by the device side control unit 46 is set in association with the emotion of the user U which is detected by the emotion detecting section 464.

In the example of FIG. 7, there are three kinds of actions set in the corresponding action table 488. That is, there are the action to be executed in a case where the emotion of the user U is usual, the action to be executed to quiet down the emotion of the user U, and the action in a case where it is judged that the emotion of the user U influences the driving.

To quiet down the emotion of the user U indicates that the emotion of the user U is returned or brought close to a normal emotion of the user U. Specifically, as shown in FIG. 6, it is indicated that the emotion of the individual personality 482, that is, the emotion of the user U is returned or brought close to the emotion of the base personality 483. In another expression, calming down, suppression, or the like can be used.

In the example of FIG. 7, an "action A-2" to quiet down the emotion in a case where the emotion of the user U is "anger" is the action that acts on to suppress and calm the anger of the user U. An "action S-2" to quiet down the emotion in a case where the emotion of the user U is "sadness" is an action that acts on to encourage the user U.

Furthermore, examples of the emotion that influences the driving include anger, anxiety, sorrow (sadness), and insecurity. The action to be executed by the device side control unit 46 in a case where these emotions are detected by the emotion detecting section 464 is an action that acts on the user U so as to quiet down and calm the emotion of the user U. To quiet down the emotion of the user U indicates that the emotion of the user U is returned or brought close to the normal emotion of the user U, and specifically indicates that the emotion is returned or brought close to the emotion of the base personality 483. In the other expression, calming-down, suppression, or the like can be used.

According to the example of FIG. 7, in the corresponding action table 488, an "action A-3" that is an action for driving in the case where the emotion of the user U is "anger" and an "action S-3" that is an action for driving in a case where the emotion of the user U is "sadness" are actions to quiet down the emotion of the user U.

Here, an action to be set in the corresponding action table 488 with respect to an emotion that is not determined to influence the driving may be doing of no actions. For example, an action for driving which is to be set in association with a case where the emotion of the user U is "insignificance" or "tiredness" may be nothing. Furthermore, an action to assist the user U in focusing on the driving may be set. For example, as the action for driving which copes with the case where the emotion of the user U is "insignificance" or "tiredness", an action that prompts the user U to focus on the driving without being bored may be set.

FIG. 8 is a diagram showing one example of contents of the action to be set in the corresponding action table 488. FIG. 8 shows, as an example, an example of a specific content of "action A-2" illustrated in the corresponding action table 488 of FIG. 7. The content that is set in FIG. 8 may be stored, for example, as the corresponding action table 488*a* that accompanies the corresponding action table 488 in the personality DB 48.

The "action A-2" acts on the user U so as to quiet down the emotion of the user U in the case where the emotion of the user U is "anger". The kinds of the action are set in "action details". That is, the device side control unit 46 performs actions of respective items of an engine output of the motorcycle 4, torque control, throttle opening limitation, an antilock brake system (ABS), the suspension setting, meter panel display, voice, and the like. These actions are executed in accordance with control of the traveling state adjustment section 465.

The respective kinds of the action set in the corresponding action tables 488 and 488*a* are executed in accordance with the control of the action control section 470. The action control section 470 controls the traveling state adjustment section 465 in accordance with the corresponding action tables 488 and 488*a*, to perform the action by the action unit 44. Furthermore, the action control section 470 controls the conversation executing section 466 in accordance with the corresponding action tables 488 and 488*a*, to perform the conversation in voice. The action control section 470 controls the output control section 467 in accordance with the corresponding action tables 488 and 488*a*, so that an action, other than the action of the action unit 44 and the conversation, can be performed.

As to the control of the engine output, the traveling state adjustment section 465 adjusts a throttle device control parameter for use by the throttle control section 412, a fuel injection map for use by the fuel injection control section 413, and an ignition timing parameter for use by the ignition control section 414. In the example of FIG. 8, the throttle device control parameter is adjusted so that the throttle opening corresponding to a throttle operation lowers, and the fuel injection map and the ignition timing parameter are adjusted so that the engine output corresponding to the throttle operation lowers. These parameters and map are stored in a storage device such as the ROM (not shown) contained in the ECU 41. The traveling state adjustment section 465 switches each parameter and map described above to another parameter and map prepared beforehand.

As to the torque control, the traveling state adjustment section 465 adjusts the fuel injection map for use by the fuel injection control section 413 and the ignition timing parameter for use by the ignition control section 414. Consequently, the fuel injection map and the ignition timing parameter are adjusted so that the output torque lowers. Concerning the throttle opening limitation, the traveling state adjustment section 465 adjusts the throttle device control parameter for use by the throttle control section 412, and an upper limit of an opening degree of the throttle valve to be opened by the throttle device 441 is lowered below, for example, a usual position. As to the ABS, the traveling state adjustment section 465 adjusts a brake control parameter for use by the brake control section 415, to change operating conditions of the ABS. Consequently, for example, the ABS operates at a speed higher than usual. As to the suspension setting, the traveling state adjustment section 465 adjusts a suspension setting adjusting parameter for use by the suspension control section 416. For example, when active suspension or semi-active suspension is mounted, the suspension adjustment section 447 of the motorcycle 4 adjusts the suspension setting, such as the damping force, the vehicle height, or the like, in accordance with the control of the suspension control section 416 during traveling or vehicle stop. The traveling state adjustment section 465 adjusts the parameter for use by the suspension control section 416, and the suspension control section 416 performs, for example, setting to attach importance to ride comfort.

As to the meter panel display, the traveling state adjustment section 465 adjusts data for use by the display control section 418, and changes the display of the meter panel 448 to a color from which an effect of relaxing the user U can be expected.

An action concerning the voice is executed by the conversation executing section 466. The conversation executing section 466 executes the conversation in voice with the user U by using the microphone 492 and the speaker 493 with reference to the conversation DB 487, and performs the conversation from which the effect of relaxing the user U can be expected. The conversation executing section 466 adjusts, for example, a pitch of the voice output from the speaker 493, a tone of the voice, a speaking speed, and a response time to the voice of the user U.

The corresponding action table 488 is not limited to the action A-2 illustrated in FIG. 8, and includes information that determines, in detail, the contents of the actions to be executed by the traveling state adjustment section 465, the conversation executing section 466, and the output control section 467 with respect to the respective actions including the example of FIG. 7.

Subsequently, an operation of the emotion inference system 1 will be described with reference to a flowchart.

FIG. 9 is a flowchart showing the operation of the emotion inference system 1, especially the operation of each device of the emotion inference system 1 during uploading of the big data 21.

The operation of FIG. 9 is executable by the respective devices of the motorcycle 4, the automobile 11, the rice cooker 12, the vacuum cleaner 13, the television receiver 14, and the refrigerator 15.

In the motorcycle 4, the device side control unit 46 executes the operation of FIG. 9. In this case, the external sensor control section 462 and the vehicle sensor control section 463 acquire the detection values of various sensors of the motorcycle 4 (step S11). The detection values detected in step S11 include the detection values detected from the microphone 492, the camera 494, the G sensor 495, and the GPS receiving section 496 by the external sensor control section 462. Furthermore, detection values of the respective sensors included in the sensor unit 43 are included in the vehicle sensor control section 463.

The communication control section 461 judges whether or not a standard is reached to upload the detection values acquired by the external sensor control section 462 and the vehicle sensor control section 463 (step S12). The upload standard can be set to, for example, every time a preset time elapses, the number of the detection values acquired in step S11, every time the detection value of the set specific sensor is acquired, or the like. When the upload standard is not reached (step S12; NO), the communication control section 461 returns to step S11, in which the external sensor control section 462 and the vehicle sensor control section 463 acquire the detection values. When the upload standard is reached (step S12; YES), the communication control section 461 transmits a connection request and the certification information to the server 3 via the communication unit 47 (step S13), and when certification is successful, transmits the detection value acquired in step S11 to the server 3.

Figure 10:
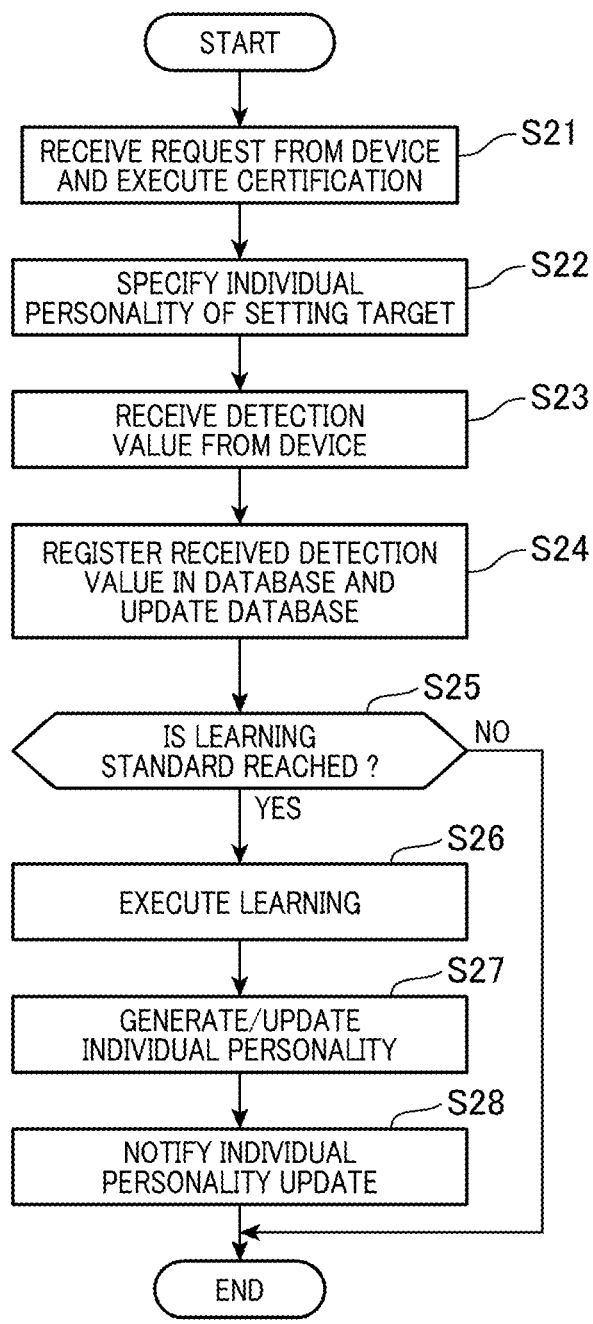
FIG. 10 is a flowchart showing an operation of a server.

FIG. 10 is a flowchart showing the operation of the server 3. The operation of FIG. 10 shows the operation concerned with reception of the detection value transmitted from the device that executes the operation of FIG. 9.

When the server side control unit 31 receives the connection request from one of the motorcycle 4, the automobile 11, the rice cooker 12, the vacuum cleaner 13, the television receiver 14, and the refrigerator 15 via the communication unit 38, the certification information is received together with the connection request, and the certification is performed by the certification processing section 313 (step S21). In step S21, the certification processing section 313 collates the certification information received by the communication unit 38 with the certification information 361 stored in the certification information storage unit 36, thereby executes the certification, and specifies the device that has made the connection request.

In the server side control unit 31, the personality forming section 311 specifies the individual personality 342 corresponding to the device certified in step S21 (step S22). Subsequently, in the server side control unit 31, the personality forming section 311 receives the detection value from the device that has succeeded in the certification in step S21 (step S23). The server side control unit 31 registers the received detection value in the personality DB 34, and updates the personality DB 34 (step S24). The server side control unit 31 analyzes the detection value received in step S23, and stores the value in the personality DB 34. For example, the server side control unit 31 extracts the data concerning the schedule of the user U from the detection value, to update the activity schedule data 344.

The server side control unit 31 registers the detection value in the personality DB 34 in step S24, and thereby judges whether or not a standard to perform the learning of the individual personality 342 is reached (step S25). The standard to perform the learning can be set to, for example, every time the preset time elapses, the number of the detection values registered in the personality DB 34 in step S24, or the like.

When the standard to perform the learning is not reached (step S25; NO), the server 3 ends the present processing.

When the standard to perform the learning is reached (step S25; YES), in the server side control unit 31, the individual personality executing section 32 executes the individual personality 342, and the learning based on the detection value registered in the personality DB 34 in step S24 is executed by the function of the machine learning provided in the individual personality 342 (step S26). Through this learning, the algorithm or parameter of the individual personality 342 is updated (step S27). Afterward, the server 3 notifies each device constituting the emotion inference system 1 that the individual personality 342 is updated (step S28), and ends the present processing.

Note that needless to say, the learning of the individual personality 342 executed in step S26 of FIG. 10 is executed by a device other than the server 3. For example, in the motorcycle 4, the device side control unit 46 may execute the learning of the individual personality 482 on the basis of the detection value detected by the sensor unit 43 and/or the external sensor 49. In this case, the motorcycle 4 may transmit the learned individual personality 482 to the server 3, and at this time, various detection values used in the learning may be transmitted as the big data 21 to the server 3.

Figure 11:
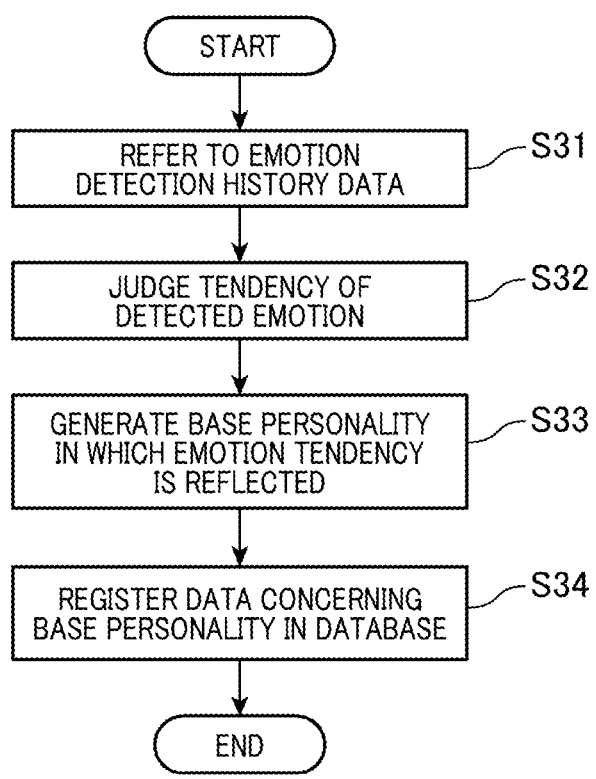
FIG. 11 is a flowchart showing an operation of the emotion inference system.

FIG. 11 is a flowchart showing the operation of the emotion inference system 1, and especially showing an operation of forming the base personality in the device constituting the emotion inference system 1. Here, processing of forming the base personality 483 in the motorcycle 4 is shown.

The base personality forming section 468 provided in the device side control unit 46 acquires the history of detection of the emotion of the user U by the emotion detecting section 464 in the past, with reference to the emotion detection history data 485 (step S31).

The base personality forming section 468 judges the tendency of the emotion of the user U on the basis of the history acquired in step S31 (step S32), and generates the base personality 483 in which the judged tendency is reflected (step S33).

The base personality forming section 468 generates data concerned with the base personality 483 generated in step S33, and registers the data in the personality DB 48 (step S34).

The base personality 483 may include a program that simulates the emotion of the user U, or data indicating the tendency of the emotion of the user U. Furthermore, in a case where the base personality 483 is the artificial intelligence, in step S33, the base personality forming section 468 executes the program including a basic algorithm of the artificial intelligence, and this algorithm of the artificial intelligence performs the machine learning of the history data acquired in step S32, thereby forming the base personality 483 suited for the user U. In this case, in step S33, a new algorithm is acquired through the machine learning, and the program and data including the algorithm acquired in step S34 are stored in the personality DB 48.

The base personality forming section 468 may repeatedly execute the operation of FIG. 11 in accordance with predetermined conditions, after the base personality 483 is formed. For example, the operation may be performed every time the device side control unit 46 transmits the detection value to the server 3.

The motorcycle 4 may not only stores the base personality 483 generated in this manner in the personality DB 48 but also transmits to the server 3. That is, in the operation described with reference to FIG. 9, the base personality 483 may be transmitted together with the detection value. In this case, the server side control unit 31 may receive the base personality 483 together with the detection value and update the base personality 343 stored in the personality DB 34 in the operation shown in FIG. 10. Then, it is notified to the other device of the emotion inference system 1 that the base personality 343 updated by the server side control unit 31 is updated, and the other device may download the updated base personality 343. In this case, a plurality of devices associated with the specific user U can share the base personality 343. Furthermore, in a case where the base personality 343 performs the learning in each device, the base personality 343 updated through the learning may be uploaded to the personality DB 34 again, and distributed to the other device.

Furthermore, the server 3 may perform the operation shown in FIG. 11. In this case, the server side control unit 31 of the server 3 may perform the operation of FIG. 11 every time the individual personality 342 is updated in the operation of FIG. 10, or every time new data is added to the big data 21. In this case, the server 3 may transmit the updated base personality 343 to each device of the emotion inference system 1, and may notify the update of the base personality 343 in the same manner as in step S28 of FIG. 10. Additionally, the operation of FIG. 11 may be executed in the device other than the server 3 and the motorcycle 4.

Figure 12:
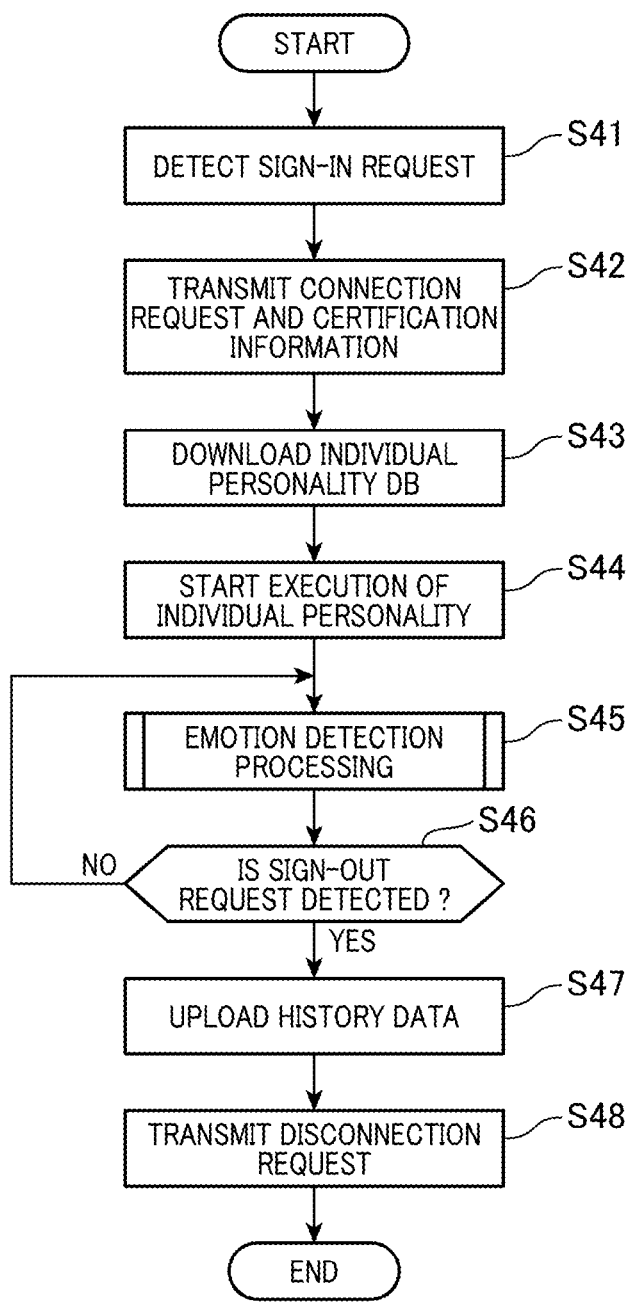
FIG. 12 is a flowchart showing an operation of the emotion inference system.
Figure 13:
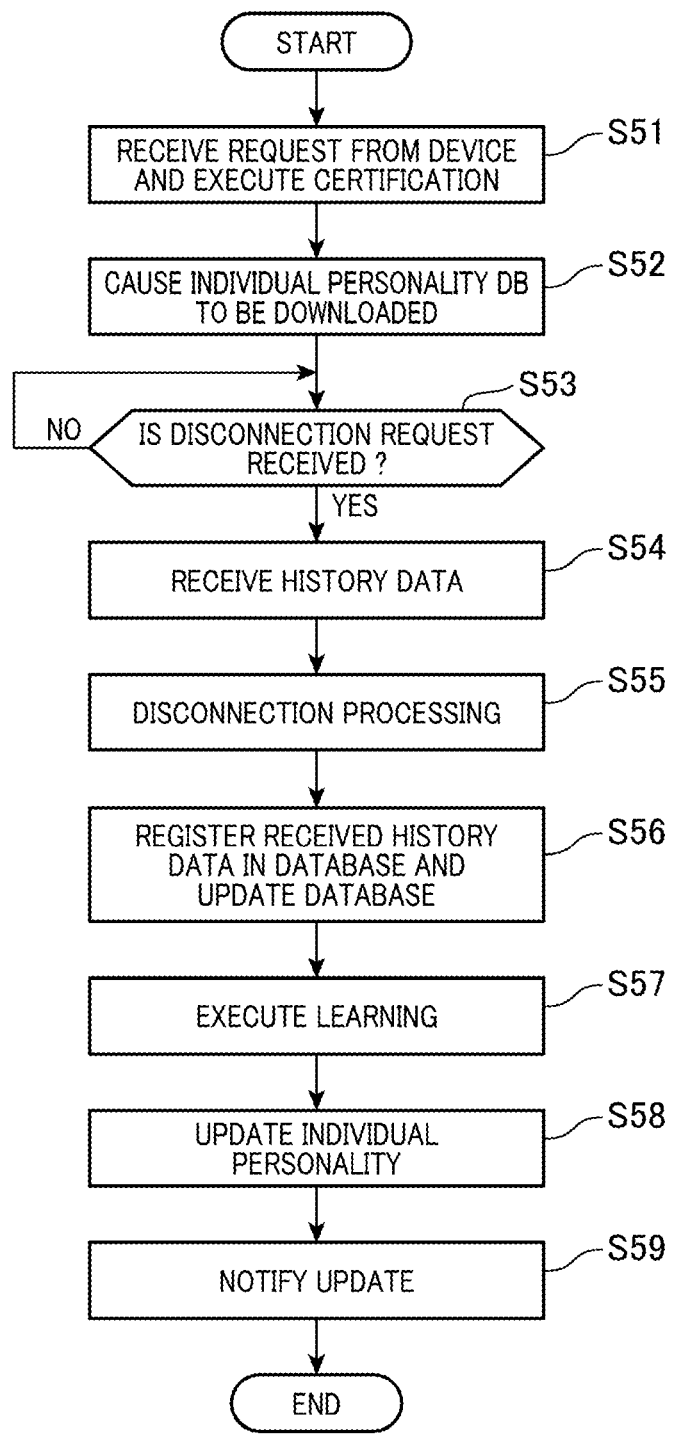
FIG. 13 is a flowchart showing an operation of the emotion inference system.

FIG. 12 is a flowchart showing an operation of the emotion inference system 1, and showing an operation to be executed by each device constituting the emotion inference system 1. FIG. 13 is a flowchart showing an operation of the server 3. Furthermore, FIG. 14 is a flowchart showing an operation of step S45 of FIG. 12 in detail.

Figure 14:
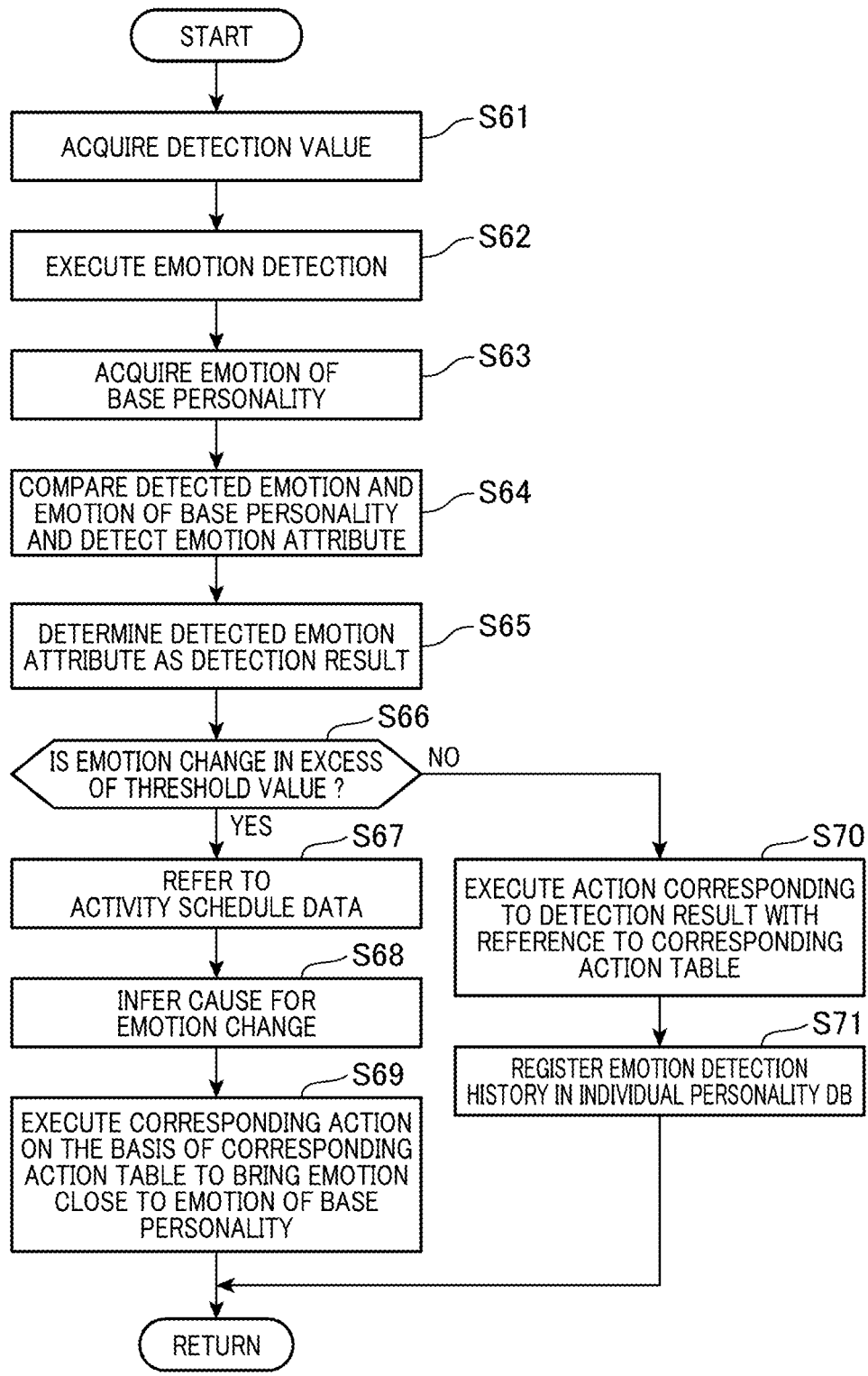
FIG. 14 is a flowchart showing an operation of the emotion inference system.

FIG. 12, FIG. 13, and FIG. 14 show an operation of downloading the personality DB 34 from the server 3 by each device constituting the emotion inference system 1, and uploading the history of the emotion detection. A main body that executes the operation of FIG. 12 and FIG. 14 may be any device excluding the server 3 in the emotion inference system 1, and here, an example where the motorcycle 4 executes the operation is described.

The operation of FIG. 12 becomes executable in a state where the user U uses the motorcycle 4. The device side control unit 46 detects a sign-in request by the user U (step S41). A specific mode of the sign-in request corresponds to, for example, instruction of sign-in in the voice by the user U. The communication control section 461 transmits the connection request and the certification information to the server 3 via the communication unit 47 (step S42), and the server 3 accordingly executes the certification.

After the certification becomes successful, the communication control section 461 downloads the personality DB 34 from the server 3 (step S43). In step S43, only a part of the program or the data contained in the personality DB 34 may be downloaded. Furthermore, when the personality DB 34 is previously downloaded and stored in the personality DB 48, only a difference between the personality DB 48 and the personality DB 34 may be downloaded in step S43.

The device side control unit 46 starts execution of the downloaded individual personality 482 (step S44). In step S44, the individual personality 482 is executed, so that the emotion of the user U can be detected. Furthermore, the device side control unit 46 starts execution of the action control section 470 in step S44. Consequently, the motorcycle 4 functions as the artificial intelligence including a concierge function to the user U.

The device side control unit 46 executes emotion detection processing of detecting the emotion of the user U by the function of the emotion detecting section 464 (step S45). Details of the emotion detection processing will be described later with reference to FIG. 14. In summary, the emotion detecting section 464 detects the emotion of the user U, and in response to this emotion, the action control section 470 controls the traveling state adjustment section 465, the conversation executing section 466, and the output control section 467, to execute the action that acts on the emotion of the user U. Furthermore, in the emotion detection processing, the emotion detection history data 485 is updated on the basis of the result of detection of the emotion of the user U by the emotion detecting section 464.

The device side control unit 46 detects a sign-out request from the user U (step S46). Although sign-out is performed, the user U can perform the driving operation of the motorcycle 4, but when the sign-out is performed, the concierge function is not executed by the individual personality 22. A specific mode of the sign-out request corresponds to, for example, instruction of the sign-out in the voice by the user U.

In a case where it is not detected that the sign-out request has been made (step S46; NO), the device side control unit 46 executes the emotion detection processing of step S45 every predetermined time.

In a case where it is detected that the sign-out request has been made (step S46; YES), in the device side control unit 46, the communication control section 461 uploads various data including the emotion detection history data 485 to the server 3 (step S47). Afterward, the communication control section 461 transmits a disconnection request to the server 3, and ends the communication with the server 3 (step S48).

The server 3 executes an operation of FIG. 13.

When the server side control unit 31 receives the connection request from one of the motorcycle 4, the automobile 11, the rice cooker 12, the vacuum cleaner 13, the television receiver 14, and the refrigerator 15 via the communication unit 38, the server side control unit receives the certification information together with the connection request, to perform certification by the certification processing section 313 (step S51). In step S51, the certification processing section 313 executes the certification by use of the certification information 361, and specifies the device that has made the connection request. Here, an example where the motorcycle 4 makes the connection request is described.

The server side control unit 31 downloads the program and data contained in the personality DB 34 to the motorcycle 4 (step S52). Here, in a case where the motorcycle 4 makes a request for a part of the program and/or the data of the personality DB 34, the server side control unit 31 transmits the program and/or the data in response to the request.

The server side control unit 31 judges whether or not the disconnection request is received from the motorcycle 4 (step S53), and is on standby while the disconnection request is not received (step S53; NO). When the disconnection request is received (step S53; YES), the server side control unit 31 receives the emotion detection history data 485 transmitted by the motorcycle 4 (step S54), and then performs processing of disconnecting the communication (session) with the motorcycle 4 (step S55). The server side control unit 31 includes and stores the data included in the emotion detection history data 485 received in step S54, in the emotion detection history data 345 of the personality DB 34, and thereby updates the personality DB 34 (step S56).

Here, the server side control unit 31 can update the individual personality 22 on the basis of the updated emotion detection history data 485. That is, the individual personality executing section 32 executes the individual personality 342, and performs learning based on the updated emotion detection history data 345, by the function of the machine learning of the individual personality 342 (step S57). The individual personality executing section 32 stores, in the personality DB 34, the individual personality 342 including an algorithm acquired anew by the learning (step S58). In step S58, the individual personality executing section 32 may update the base personality 343 by the function of the updated individual personality 342.

The server side control unit 31 notifies each device constituting the emotion inference system 1 that the individual personality 342 is updated (step S59), and ends the present processing.

Furthermore, the server side control unit 31 may update the concierge personality 23 together with the update of the individual personality 22.

Furthermore, in FIG. 14, in the emotion detecting section 464, the external sensor control section 462 and the vehicle sensor control section 463 acquire the detection values (step S61). The emotion detecting section 464 executes the detection of the emotion of the user U on the basis of the acquired detection values (step S62). For example, the emotion detecting section 464 provides, to the individual personality 482, the detection values acquired by the external sensor control section 462 and the vehicle sensor control section 463, and detects the emotion or the emotion change of the individual personality 482. The emotion of the individual personality 482 imitates the emotion of the user U, so that the emotion detecting section 464 can infer the emotion of the user U by detecting the emotion of the individual personality 482. The emotion detecting section 464 executes the base personality 483 of the personality DB 48, to acquire the emotion of the base personality 483 (step S63).

The emotion detecting section 464 compares the emotion of the user U which is detected in step S62 with the emotion of the base personality 483 which is acquired in step S63, and thereby detects the emotion attribute (step S64). The operation of step S64 is performed as described with reference to, for example, FIG. 6. The emotion attribute is the emotion of the user U corrected by additionally taking the normal emotion of the user U into consideration. The emotion of the user U at the normal time can be inferred as the emotion of the base personality 483.

The emotion detecting section 464 determines the emotion attribute detected in step S64 as the detection result of the emotion of the user U (step S65).

Here, in the device side control unit 46, the emotion change cause inferring section 469 judges the emotion change of the user U which is detected by the emotion detecting section 464 (step S66). In step S66, the emotion change cause inferring section 469 compares the judgment result of the emotion of the user U with the judgment result of the emotion detected before, i.e., in the past, to judge whether or not there is an emotion change in excess of a set threshold value. Here, it is preferable that the emotion change cause inferring section 469 compares the detection result of the emotion detected and determined by the emotion detecting section 464 with the immediately previously judged emotion of the user U. The detection result of the emotion of the user U which is detected by the emotion detecting section 464 can be acquired from the emotion detection history data 485.

When it is judged that there is the emotion change in excess of the threshold value (step S66; YES), the emotion change cause inferring section 469 refers to the activity schedule data 484 (step S67). The emotion change cause inferring section 469 extracts the future schedule of the user U from the schedule included in the activity schedule data 484, and infers the schedule that is a factor for the emotion change (step S68). The emotion change cause inferring section 469 infers, as the cause for the emotion change, for example, a schedule having a high demand and/or a high emergency or a schedule having a low free degree of changeability in the future schedule included in the activity schedule data 484.

The traveling state adjustment section 465, the conversation executing section 466, and the output control section 467 execute the corresponding actions on the basis of the cause inferred in step S68 and the detection result of the emotion of the user U which is determined in step S65, so as to bring the emotion of the user U close to the emotion of the base personality 483 (step S69). The corresponding actions executed here are the actions set in the corresponding action table 488. In consequence, the motorcycle 4 can act on the emotion of the user U to quiet down the emotion. Furthermore, the motorcycle 4 infers the factor for the emotion change of the user U, and acts on the emotion to cope with this factor, so that the emotion of the user U can be effectively quieted down. Furthermore, in step S68, when there is not any schedule that can be the factor for the emotion change of the user U, the motorcycle 4 may act on the user U in step S69 on the assumption that there are not any corresponding schedules.

Additionally, when it is judged that there is not any emotion change in excess of the threshold value (step S66; NO), the traveling state adjustment section 465, the conversation executing section 466, and the output control section 467 execute the corresponding actions on the basis of the detection result of the emotion of the user U which is determined in step S65 (step S70). The corresponding actions executed here are the actions set in the corresponding action table 488. Afterward, the emotion detecting section 464 registers the detection result determined in step S65 in the emotion detection history data 485 (step S71). Note that the action may shift to step S71 after the action of step S69.

Figure 15:
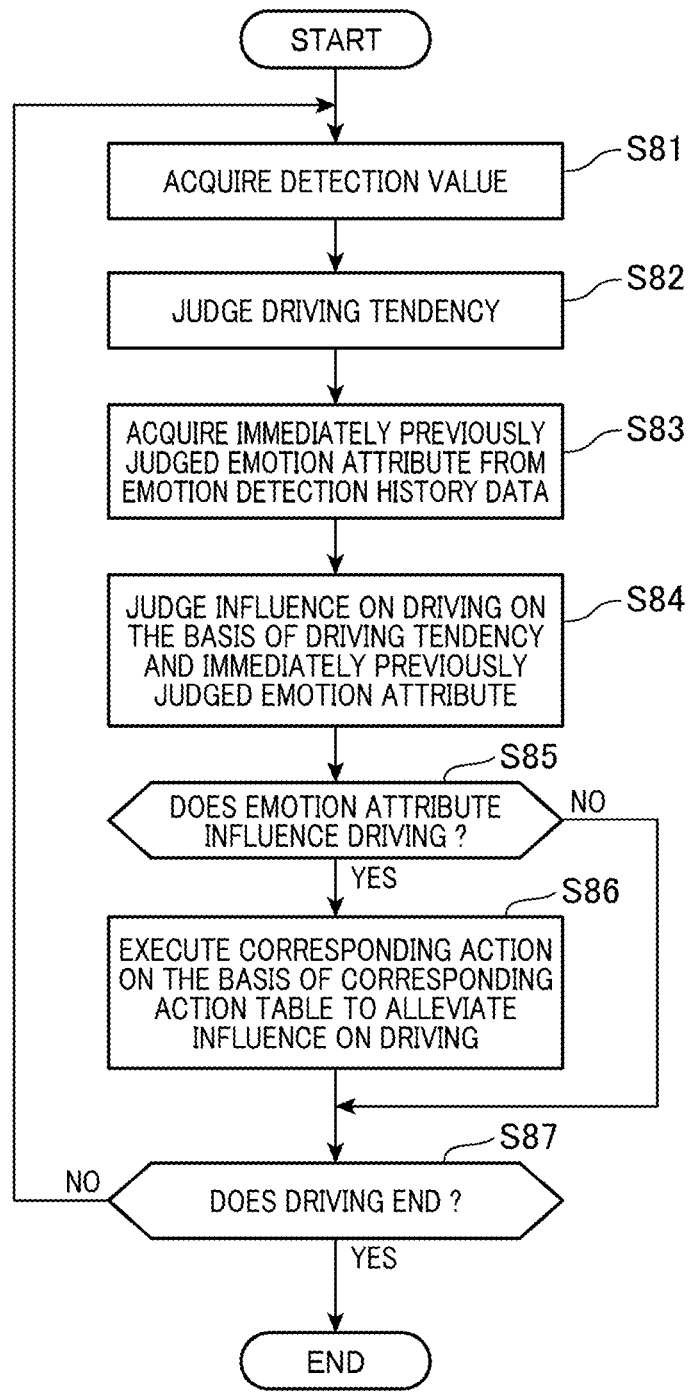
FIG. 15 is a flowchart showing an operation of the emotion inference system.

FIG. 15 is a flowchart showing an operation of the device constituting the emotion inference system 1, and showing an operation of assisting the user U so that the emotion of the user U who is a driver does not obstruct the driving. The operation of FIG. 15 can be executed by the motorcycle 4 and the automobile 11. Here, an example of the execution by the motorcycle 4 is described.

The motorcycle 4 executes the operation of FIG. 15, while the user U drives the motorcycle 4. At the start of the operation of FIG. 15, in the motorcycle 4, the device side control unit 46 executes the individual personality 482.

In the device side control unit 46, the external sensor control section 462 and the vehicle sensor control section 463 acquire the detection values of the respective sensors provided in the motorcycle 4 (step S81). The emotion detecting section 464 judges a driving tendency from the detection value acquired in step S81 (step S82). In step S82, the emotion detecting section 464 judges at least whether the driving tendency of the user U is "patient driving" or "impatient driving". Furthermore, the emotion detecting section 464 can judge that the driving does not correspond to either "the patient driving" or "the impatient driving", and can further judge that the driving is another driving. The emotion detecting section 464 provides, to the individual personality 482, the detection values acquired by the external sensor control section 462 and the vehicle sensor control section 463, and detects the emotion of the individual personality 482, so that it may be judged that the driving is "the patient driving" or "the impatient driving".

The emotion detecting section 464 acquires the emotion attribute of the user U judged in the past (especially, the emotion attribute judged immediately before the judgment of step S82) with reference to the emotion detection history data 485 (step S83). The emotion detecting section 464 judges presence or absence of the influence exerted on the driving by the emotion of the user U on the basis of the judgment result of the driving tendency in step S82 and the emotion attribute acquired in step S83 (step S84). In consequence, it is judged whether the current emotion of the user U is the emotion that influences the driving of the motorcycle 4.

When the emotion detecting section 464 judges that the emotion of the user U influences the driving (step S85; YES), the action control section 470 controls the traveling state adjustment section 465, the conversation executing section 466, and the output control section 467 in accordance with the setting of the corresponding action table 488 (step S86). Consequently, the motorcycle 4 can act on the user U so as to change the emotion of the user U to the emotion that does not influence the driving. Afterward, the device side control unit 46 judges whether or not the user U ends the driving operation (step S87). When the driving ends (step S87; YES), the operation of FIG. 15 ends. Furthermore, when the driving continues (step S87; NO), the operation returns to step S81.

Additionally, when the emotion detecting section 464 judges that the emotion of the user U does not influence the driving (step S85; NO), the device side control unit 46 shifts to step S87.

In the above embodiment, the configuration has been illustrated in which the motorcycle 4 includes the device side control unit 46, the personality DB 48, and the external sensor 49, in addition to a function unit and an action unit for travelling which include the ECU 41, the sensor unit 43, and the action unit 44.

Here, there is shown a configuration example where a general motorcycle is combined with a mobile terminal device such as a smartphone, to operate as the motorcycle 4.

Figure 16:
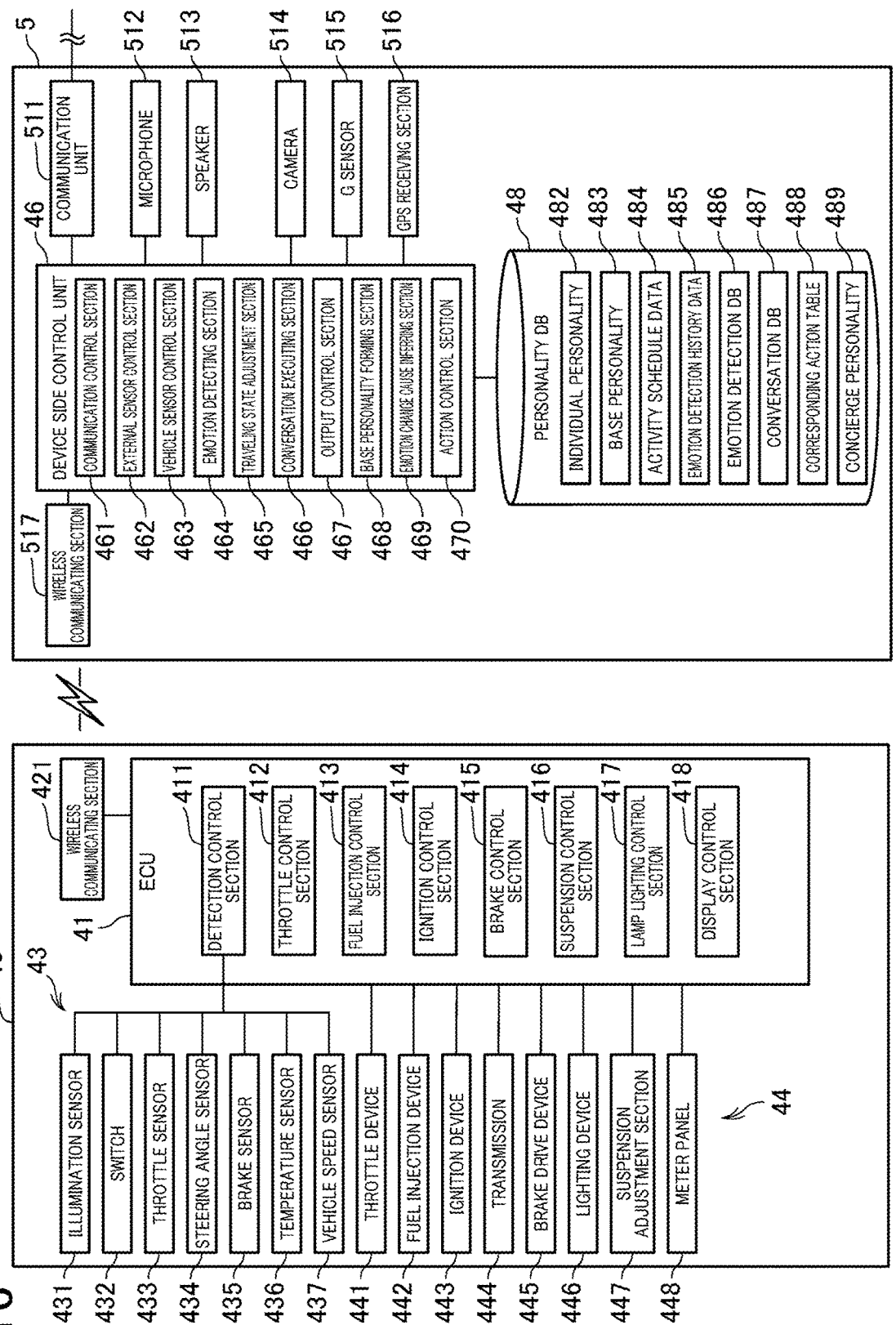
FIG. 16 is a function block diagram showing another configuration example of the motorcycle.

FIG. 16 is a function block diagram showing a motorcycle 40 and a mobile terminal device 5, as another configuration example of the motorcycle 4.

The motorcycle 40 has a function unit and an action unit which are required for traveling in the motorcycle 4 described above. Specifically, as shown in FIG. 16, the motorcycle 40 includes an ECU 41, a sensor unit 43, and an action unit 44. Note that the same constituting part as in the motorcycle 4 shown in FIG. 4 is denoted with the same reference signs and description is omitted.

Furthermore, the motorcycle 40 includes a wireless communicating section 421. The wireless communicating section 421 performs short-range communication by utilizing at least a short-range wireless communication protocol. For example, the wireless communicating section 421 performs wireless communication which is compatible with Bluetooth, IrDA, RFID, IEEE 802.11 (so-called wireless LAN), and the like.

The mobile terminal device 5 is a device such as a smartphone, a mobile phone, or a tablet computer which is possessed or used by a user U. The mobile terminal device 5 includes a processor and a storage device functioning as a device side control unit 46 and a personality DB 48 in the same manner as in the motorcycle 4 (FIG. 4).

Furthermore, the mobile terminal device 5 includes a communication unit 511, a microphone 512, and a speaker 513. The communication unit 511 is connected to a wireless telephone line to execute communication, and can be connected to a communication network 2 via this wireless telephone line. The microphone 512 collects voice of the user U, and the speaker 513 outputs the voice in accordance with control of the device side control unit 46. The speaker 513 may be an earphone to be attached to an ear of the user U.

The communication unit 511 may be a communication unit for use in executing a telephone call and data communication by the mobile terminal device 5 as a mobile telephone set or the smartphone. The microphone 512 and the speaker 513 may input and output the voice for the telephone call.

The mobile terminal device 5 includes a camera 514, a G sensor 515, and a GPS receiving section 516. These components can have similar configurations to the camera 494, the G sensor 495, and the GPS receiving section 496 shown in FIG. 4.

The mobile terminal device 5 includes a wireless communicating section 517. The wireless communicating section 517 is configured similarly to the wireless communicating section 497 (FIG. 4), and performs short-range communication by utilizing at least a short-range wireless communication protocol. For example, the wireless communicating section 517 performs wireless communication which is compatible with Bluetooth, IrDA, RFID, IEEE 802.11 (so-called wireless LAN), and the like.

The wireless communicating section 517 executes wireless communication between the wireless communicating section 421 provided in the motorcycle 40 and the wireless communicating section 517.

The configuration shown in FIG. 16 achieves a configuration in which the motorcycle 40 is connected to the device side control unit 46 and the personality DB 48 provided in the mobile terminal device 5 by the wireless communication between the wireless communicating section 421 and the wireless communicating section 517. Therefore, a function and an operation similar to those of the motorcycle 4 described in the above embodiment can be executed by the motorcycle 40 together with the mobile terminal device 5.

The ECU 41 has a function of transmitting a detection value and the like detected by the sensor unit 43 to the mobile terminal device 5 via the wireless communicating section 421, and a function of operating the action unit 44 on the basis of data received by the wireless communicating section 421. Except this regard, the motorcycle 40 has a configuration of the general motorcycle.

In the configuration of FIG. 16, a basis of the motorcycle 40 is combined with the mobile terminal device 5 for use by the user U, so that a device that assists the user U can be achieved on the basis of artificial intelligence similarly to the motorcycle 4 (FIG. 4).

As described above, the motorcycle 4 that is the emotion inference device of the embodiment to which the present invention is applied includes the individual personality 482 configured on the basis of the information concerning the user U from the plurality of products associated with the user U which are connected to the communication network 2. In the emotion inference system 1, the individual personality 482 forms the base personality 483. Furthermore, the motorcycle 4 includes the emotion detecting section 464 that detects the emotion.

In another expression, there is included the individual personality 482 formed by the machine learning based on the user information collected from the plurality of products used by the user U. The device side control unit 46 that executes the individual personality 482 forms the base personality 483. The device is not limited to the device side control unit 46, and, for example, in the server side control unit 31, the individual personality 342 may form the base personality 343. Then, the device side control unit 46 includes the emotion detecting section 464 that detects the emotion of the user U. The emotion detecting section 464 may be implemented as the function of the individual personality 482, or may be as another function.

In consequence, the emotion can be detected with high precision by the individual personality 482 that is configured on the basis of the information from the plurality of products. For example, the emotion inference system 1 has, as the plurality of products which differ in time to use by the user U, the motorcycle 4, the automobile 11, the rice cooker 12, the vacuum cleaner 13, the television receiver 14, and the refrigerator 15. In the emotion inference system 1, the individual personality 482 is formed by using the information from the plurality of products, and hence the individual personality 482 is a personality in which the characteristic of the user U is reflected with high precision. Therefore, when the emotion of the user U is detected by utilizing the individual personality 482, the information collected or detected for a longer period of time is used as compared with a case where a single product infers the emotion of the user U, and the emotion can be detected with higher precision as compared with a case where the detection is based on the information obtained from the single product. Furthermore, as to a specific product, the emotion before the product is associated with the user U can be also detected.

The emotion detecting section 464 compares the emotion of the base personality 483 with the emotion of the individual personality 482 at the moment, and detects the emotion attribute. The emotion of the user U can be detected with higher precision by using the emotion of the base personality as a reference and additionally taking the tendency and characteristic of the emotion of the user U into consideration. For example, in a case where there is a tendency that a specific emotion easily appears in the emotion of the user U, it is possible to avoid a state where the specific emotion is frequently detected. Therefore, it is possible to detect the emotion with high precision by use of a standard adapted to an individual emotion tendency.

The motorcycle 4 includes the action control section 470 that controls the action to direct the emotion to the emotion of the base personality 483 when the predetermined change or greater is present in the emotion detected by the emotion detecting section 464. Consequently, the individual personality 482 performs the action which directs the emotion of the user U to the emotion of the base personality 483, and can act on the emotion of the user U in consideration of the tendency and characteristic of the emotion of the user U. In consequence, for example, the emotion of the user U can be calmed down.

The motorcycle 4 further includes the emotion detection history data 485 that accumulates the emotion detected by the emotion detecting section 464, and the activity schedule data 484 showing the activity schedule of the user U. The device side control unit 46 which executes the individual personality 482 includes the emotion change cause inferring section 469. The emotion change cause inferring section 469 infers the emotion change cause from at least the emotion accumulated in the emotion detection history data 485 and the future schedule shown in the activity schedule data 484 of the user U, when there is a large change in the emotion of the user U. Consequently, the cause that changes the emotion of the user U or the cause that influences the emotion can be inferred from the future schedule. In consequence, it is possible to cope with the cause that changes the emotion or the cause that influences the emotion so that the emotion of the user U is influenced.

Furthermore, in the motorcycle 4, the cause inferred by the emotion change cause inferring section 469 is also accumulated when accumulating the emotion in the emotion detection history data 485. Consequently, data concerning the tendency of the emotion of the user U and the cause can be collected by accumulating the cause that changes the emotion of the user U or the cause that influences the emotion. The collected data can be utilized as data to be learned by the processor (the computer) that functions, for example, as the emotion detecting section 464.

Additionally, the action control section 470 copes with the cause inferred by the emotion change cause inferring section 469, and executes an action that directs the emotion back to the emotion of the base personality 483. Consequently, it is possible to more effectively act on the emotion of the user U on the basis of the cause that changes the emotion of the user U or the cause that influences the emotion.

In the above embodiment, the emotion inference system 1 includes the plurality of products, and one of these products is the motorcycle 4 or 40. In the motorcycle 4 or 40, the emotion detecting section 464 judges the driving tendency. The emotion detecting section 464 distinguishes at least between the patient driving and the impatient driving. In a case where it is judged that the driving of the user U is the impatient driving, it is judged whether or not the emotion influences the driving, from at least an immediately prior emotion and the activity schedule shown in the activity schedule data 484 of the user U. In a case where the emotion detecting section 464 judges that the driving is influenced, the action control section 470 performs an action that directs the emotion so as to eliminate the influence on the driving. Thus, the action control section 470 acts on the user U, so that it is possible to achieve the elimination or alleviation of the factor that influences the driving of the vehicle.

Here, the emotion that influences the driving may include any one of anger, anxiety, sorrow, and insecurity. Consequently, in a case where it is detected that the emotion of the user U is an emotion such as the anger, the anxiety, the sorrow, or the insecurity, it is possible to achieve elimination or alleviation of an influence of such an emotion on the driving.

Furthermore, the individual personality 482 that is the artificial intelligence is configured on the basis of the information from the plurality of products, and hence the emotion can be detected with high precision by the individual personality 482.

Additionally, the individual personality (482) imitates the emotion or emotion change of the user (U), and the emotion detecting section (464) detects the emotion of the individual personality (482). Consequently, the emotion or emotion change of the user U can be easily detected by detecting the emotion of the individual personality 482. Furthermore, the individual personality 482 is configured on the basis of the information from the plurality of products, so that the user's emotion can be detected with higher precision.

Note that the above embodiment indicates one aspect to which the present invention is applied, and the present invention is not limited to the above embodiment.

In the above embodiment, the motorcycle 4 or 40 has been described as one example of the vehicle, but the present invention is not limited to this example. For example, the present invention is applicable to a saddle vehicle of three wheels including two front or rear wheels, a saddle vehicle including four or more wheels, and a saddle vehicle such as a scooter. Furthermore, the motorcycle 4 or 40 shows one example of the motorcycle, and the motorcycle to which the present invention is applied is not restricted. For example, the sensor provided in the motorcycle 4 or 40 is not limited to the sensor unit 43, and a sensor that detects a suspension stroke amount may be provided, a pressure sensor may be provided in a suspension or a brake, and acceleration sensors may be provided in a plurality of regions of a vehicle body, so that movement of the motorcycle 4 is detected in more detail. Furthermore, the present invention is also applicable to the motorcycle that does not include a part of the sensor unit 43 or the action unit 44.

Furthermore, the motorcycle 4, 40, the automobile 11, the rice cooker 12, the vacuum cleaner 13, the television receiver 14, or the refrigerator 15 is one example shown as the device to which the present invention is applicable, and needless to say, the present invention is also applicable to another type of device.

Additionally, the function block shown in each of FIG. 3, FIG. 4, and FIG. 16 shows a functional configuration achieved by cooperation of hardware and software. Specific implementations of the respective devices are not limited to the above block diagrams. Therefore, it is not necessary to individually implement corresponding hardware to each function part in the function block diagram, and needless to say, one processor may be configured to execute a program to achieve a plurality of functions of function parts. Additionally, in the above embodiment, a part of the function achieved by the software may be achieved by the hardware, or a part of the function achieved by the hardware may be achieved by the software. Alternatively, the function can be configured on the basis of programmed hardware. Additionally, a specific detailed configuration of another part of the emotion inference system 1 can be also arbitrarily changed without departing from the gist of the present invention.

REFERENCE SIGNS LIST

1 emotion inference system
2 communication network
3 server
4 motorcycle (emotion inference device)
5 mobile terminal device
11 automobile (emotion inference device)
12 rice cooker (emotion inference device)
13 vacuum cleaner (emotion inference device)
14 television receiver (emotion inference device)
15 refrigerator (emotion inference device)
21 big data
22 individual personality
23 concierge personality
31 server side control unit
32 individual personality executing section
40 motorcycle (emotion inference device)
46 device side control unit
48 personality DB
464 emotion detecting section (driving tendency judging section)
468 base personality forming section
469 emotion change cause inferring section
470 action control section
482 individual personality
483 base personality
484 activity schedule data (activity schedule table)
485 emotion detection history data (emotion accumulation unit)
489 concierge personality

The invention claimed is:

1. An emotion inference device that is connected, through a communication network, to a plurality of products associated with a user, and that comprises a processor and a memory, wherein
the memory stores:
information on the user received from the plurality of products through the communication network;
an individual personality that is an algorithm to imitate, by machine learning the information, an emotion or emotion change, of the user, that copes with an external factor; and
a base personality that is formed by the individual personality and that is the emotion of the user in a calm state,
the processor functions as an emotion detecting section that detects the emotion of the user by comparing the emotion or emotion change, of the user, that copes with the external factor and that is formed by executing the individual personality, and the base personality, and
the processor functions as an action control section that controls an action to direct the emotion, of the user, based on the emotion of the user in case deviation between the emotion estimated by the emotion detecting section and the base personality exceeds a predetermined range.

2. The emotion inference device according to claim 1, wherein the memory comprises:
an emotion accumulation unit that accumulates the emotion, of the user, detected by the emotion detecting section as an emotion detection history data, and
an activity schedule table that shows an activity schedule data concerning a future schedule of the user,
the processor functions as an emotion change cause inferring section that infers a cause of change in an emotion of the user from at least the emotion detection history data accumulated in the emotion accumulation unit or the future schedule shown in the activity schedule table of the user, when there is a large change in the emotion of the user.

3. The emotion inference device according to claim 2, wherein the cause of change in the emotion of the user inferred by the emotion change cause inferring section is accumulated when accumulating the emotion, of the user, in the emotion accumulation unit.

4. The emotion inference device according to claim 2, wherein the action control section copes with the cause of change in the emotion of the user inferred by the emotion change cause inferring section, and controls an action that directs the emotion of the user.

5. The emotion inference device according to claim 4, wherein the emotion inference device is mounted on a vehicle,
the processor functions as a driving tendency judging section that judges a driving tendency of the vehicle,
the driving tendency judging section distinguishes at least between patient driving and impatient driving, and
judges whether or not a current emotion of the user influences the driving of the vehicle, from at least an immediately prior emotion of the user and the activity schedule shown in the activity schedule table of the user, when a detection value showing that the driving of the user is judged as the impatient driving is acquired from a sensor, and
when the driving tendency judging section judges that the driving is influenced, the processor, by the action control section, directs to the emotion of the user so as to eliminate the influence on the driving.

6. The emotion inference device according to claim 5, wherein the emotion that influences the driving includes one of anger, anxiety, sorrow, and insecurity.

7. An emotion inference system comprising:
a vehicle connected to a communication network, and
a plurality of products associated with a user and connected to the communication network, wherein
the vehicle comprises a processor and a memory,
the memory stores:
information on the user received from the plurality of products through the communication network;
an individual personality that is an algorithm to imitate, by machine learning the information, an emotion or emotion change, of the user, that copes with an external factor; and
a base personality that is formed by the individual personality and that is the emotion of the user in a calm state,
the processor functions as an emotion detecting section that detects an emotion of the user by comparing the emotion or emotion change, of the user, that copes with the external factor and that is formed by executing the individual personality, and the base personality, and
the processor functions as an action control section that controls an action to direct the emotion, of the user, based on the emotion of the user in case deviation between the emotion estimated by the emotion detecting section and the base personality exceeds a predetermined range.

* * * * *